US011680218B2

(12) United States Patent
Hunt et al.

(10) Patent No.: US 11,680,218 B2
(45) Date of Patent: Jun. 20, 2023

(54) BIODEGRADABLE LUBRICANT WITH TAILORED HYDROLYTIC STABILITY AND IMPROVED THERMAL STABILITY THROUGH ALKOXYLATION OF GLYCEROL

(71) Applicant: Tetramer Technologies, LLC, Pendleton, SC (US)

(72) Inventors: Zachary J. Hunt, Simpsonville, SC (US); Benjamin F. Bergmann, Liberty, SC (US); Monika Mujkic, Seneca, SC (US); Jeffrey R. DiMaio, Central, SC (US)

(73) Assignee: Tetramer Technologies, LLC, Pendleton, SC (US)

( * ) Notice: Subject to any disclaimer, the term of this patent is extended or adjusted under 35 U.S.C. 154(b) by 0 days.

(21) Appl. No.: 17/115,934

(22) Filed: Dec. 9, 2020

(65) Prior Publication Data

US 2021/0171851 A1 Jun. 10, 2021

Related U.S. Application Data

(63) Continuation-in-part of application No. 16/429,184, filed on Jun. 3, 2019, now Pat. No. 11,230,682.

(60) Provisional application No. 62/680,030, filed on Jun. 4, 2018.

(51) Int. Cl.

| | |
|---|---|
| ***C10M 105/44*** | (2006.01) |
| ***C07C 69/604*** | (2006.01) |
| ***C07C 69/675*** | (2006.01) |
| *C10N 20/02* | (2006.01) |
| *C10N 30/10* | (2006.01) |
| *C10N 30/08* | (2006.01) |

(52) U.S. Cl.

CPC ......... *C10M 105/44* (2013.01); *C07C 69/604* (2013.01); *C07C 69/675* (2013.01); *C10M 2207/3025* (2013.01); *C10M 2207/345* (2013.01); *C10N 2020/02* (2013.01); *C10N 2030/08* (2013.01); *C10N 2030/10* (2013.01)

(58) Field of Classification Search

CPC ........ C10M 105/44; C10M 2207/3025; C10M 2207/345; C10M 2207/2825; C10M 2207/2835; C10M 2207/2895; C10M 2209/1033; C10M 2209/1045; C10M 2209/1055; C10M 107/34; C10M 105/38; C07C 69/604; C07C 69/675; C07C 69/33; C07C 69/30; C10N 2020/02; C10N 2030/08; C10N 2030/10; C10N 2020/011; C10N 2020/017; C10N 2020/04; C10N 2020/081; C10N 2030/06; C10N 2030/12; C10N 2030/20; C10N 2030/64; C10N 2040/04; C10N 2040/08; C10N 2040/16; C10N 2050/10

USPC .......................................................... 508/463

See application file for complete search history.

(56) References Cited

U.S. PATENT DOCUMENTS

| | | | | |
|---|---|---|---|---|
| 3,337,595 | A | 8/1967 | Lamont | |
| 3,530,070 | A | 9/1970 | Rosevear et al. | |
| 3,871,837 | A | 3/1975 | Bedague et al. | |
| 4,031,118 | A | 6/1977 | Miller | |
| 4,983,329 | A | 1/1991 | Cooper | |
| 5,494,693 | A | 2/1996 | Cooper | |
| 5,571,935 | A | 11/1996 | Sekula et al. | |
| 5,618,779 | A | 4/1997 | Klein et al. | |
| 5,645,881 | A | 7/1997 | Tancibok et al. | |
| 5,681,939 | A | 10/1997 | Ferenz | |
| 5,916,854 | A * | 6/1999 | Inaya .................. | C10M 111/00 508/452 |
| 6,002,030 | A | 12/1999 | Valbert | |
| 6,268,010 | B1 | 7/2001 | Sekula | |
| 9,011,961 | B2 | 4/2015 | Strecker et al. | |
| 2003/0072864 | A1 | 4/2003 | Sekula | |
| 2011/0247578 | A1 | 10/2011 | Jansson et al. | |
| 2018/0010060 | A1 | 1/2018 | Zannoni et al. | |
| 2019/0367831 | A1 | 12/2019 | Hunt et al. | |

FOREIGN PATENT DOCUMENTS

| | | |
|---|---|---|
| EP | 0353928 A2 | 2/1990 |
| WO | WO1995002659 | 1/1995 |
| WO | WO2012134792 | 10/2012 |
| WO | WO2012158503 | 11/2012 |
| WO | WO2014124698 | 8/2014 |

OTHER PUBLICATIONS

Anonymous, Polysorbate, Wikipedia, May 24, 2017, URL:https://en.wikipedia.org/wiki/Polysorbate.

* cited by examiner

*Primary Examiner* — Prem C Singh
*Assistant Examiner* — Francis C Campanell
(74) *Attorney, Agent, or Firm* — Burr & Forman LLP; Douglas L. Lineberry

(57) ABSTRACT

Described herein are methods of stabilizing the beta hydrogen of glycerol based esters by the insertion of alkoxy groups to significantly improve the thermal, oxidative, and hydrolytic stability of the ester and allow for controlling the molar density of esters bonds in the lubricants to maximize hydrolytic stability while maintaining biodegradability and further improving performance properties.

20 Claims, 27 Drawing Sheets

Table A. Examples 1-24

| | Example | Pour Point (°C) | Kinematic Viscosity | | | Fatty Acid Content | | | |
|---|---|---|---|---|---|---|---|---|---|
| | | | KV 40 | KV 100 | VI | C-12 | C-14 | C-16 | C-18 |
| PG-10 | 1 | 7.18 | 67.65 | 12.5 | 186 | 0.0000 | 0.3181 | 0.3392 | 0.3426 |
| | 2 | -11.07 | 58.05 | 11 | 185 | 0.0000 | 0.9801 | 0.0044 | 0.0154 |
| | 3 | -37.52 | 53.65 | 9.9 | 173 | 0.9693 | 0.0115 | 0.0000 | 0.0192 |
| | 4 | -9.82 | 59.1 | 10.9 | 179 | 0.3035 | 0.3377 | 0.3488 | 0.0099 |
| | 5 | 15.22 | 69.5 | 12.5 | 181 | 0.0000 | 0.0000 | 0.4817 | 0.5183 |
| | 6 | -0.97 | 61.15 | 11.4 | 183 | 0.3169 | 0.3342 | 0.0087 | 0.3403 |
| | 7 | -38.32 | 55 | 10.25 | 178 | 0.9862 | 0.0138 | 0.0000 | 0.0000 |
| | 8 | 10.56 | 74 | 13.2 | 182 | 0.1212 | 0.1299 | 0.1279 | 0.6210 |
| | 9 | -25.12 | 58.4 | 10.8 | 179 | 0.4904 | 0.5016 | 0.0040 | 0.0039 |
| | 10 | 20.62 | 76.85 | 13.4 | 179 | 0.0000 | 0.0000 | 0.0077 | 0.9923 |
| | 11 | -7.9 | 64.9 | 11.7 | 178 | 0.1230 | 0.6201 | 0.1267 | 0.1302 |
| | 12 | 3.07 | 68.5 | 12.3 | 180 | 0.1138 | 0.1258 | 0.6183 | 0.1422 |
| | 13 | -23.67 | 56 | 10.5 | 180 | 0.4840 | 0.4982 | 0.0043 | 0.0136 |
| | 14 | -12.72 | 59.7 | 11 | 179 | 0.6098 | 0.1324 | 0.1289 | 0.1290 |
| | 15 | -13.04 | 60.3 | 11.1 | 179 | 0.0112 | 0.9836 | 0.0052 | 0.0000 |
| | 16 | -0.72 | 63.4 | 11.6 | 180 | 0.0042 | 0.4839 | 0.4941 | 0.0178 |
| | 17 | 8.37 | 68 | 12.3 | 181 | 0.0058 | 0.4872 | 0.0108 | 0.4962 |
| | 18 | 1.1 | 64.6 | 11.8 | 181 | 0.2462 | 0.2637 | 0.2503 | 0.2398 |
| | 19 | -5.81 | 58.6 | 9.9 | 155 | 0.4670 | 0.0000 | 0.5131 | 0.0199 |
| | 20 | 8.97 | 63.2 | 11.6 | 181 | 0.0000 | 0.0000 | 0.9750 | 0.0250 |
| | 21 | 21.96 | 72.7 | 13.2 | 186 | 0.0000 | 0.0000 | 0.0000 | 1.0000 |
| | 22 | 8.31 | 65.35 | 12 | 183 | 0.0000 | 0.0000 | 0.9679 | 0.0321 |
| | 23 | 6.35 | 61.85 | 11.5 | 183 | 0.4795 | 0.0000 | 0.0110 | 0.5095 |
| | 24 | 7.69 | 62.8 | 11.5 | 180 | 0.3095 | 0.0000 | 0.3419 | 0.3487 |

FIGURE 3

Table B. Examples 25-48

| | Example | Pour Point (°C) | Kinematic Viscosity | | | Fatty Acid Content | | | |
|---|---|---|---|---|---|---|---|---|---|
| | | | KV 40 | KV 100 | VI | C-12 | C-14 | C-16 | C-18 |
| PG-05 | 25 | 16.77 | 57.25 | 10.5 | 175 | 0.0000 | 0.3155 | 0.3330 | 0.3514 |
| | 26 | 1.08 | 48.9 | 9.2 | 173 | 0.0000 | 0.9858 | 0.0142 | 0.0000 |
| | 27 | -19.74 | 40.8 | 7.9 | 169 | 0.9718 | 0.0282 | 0.0000 | 0.0000 |
| | 28 | 0.07 | 47.2 | 8.9 | 172 | 0.3443 | 0.3319 | 0.3238 | 0.0000 |
| | 29 | 24.11 | 61.7 | 11.2 | 177 | 0.0000 | 0.0000 | 0.4839 | 0.5161 |
| | 30 | 8.76 | 50.4 | 9.5 | 176 | 0.3129 | 0.3322 | 0.0174 | 0.3376 |
| | 31 | -21.3 | 40.15 | 7.9 | 173 | 0.9646 | 0.0198 | 0.0000 | 0.0156 |
| | 32 | 22.7 | 57.95 | 10.5 | 173 | 0.1198 | 0.1210 | 0.1251 | 0.6341 |
| | 33 | -10.02 | 43.1 | 8.45 | 177 | 0.4985 | 0.5015 | 0.0000 | 0.0000 |
| | 34 | 30.69 | | | | 0.0000 | 0.0000 | 0.0080 | 0.9920 |
| | 35 | 5.01 | 48 | 9.2 | 178 | 0.1241 | 0.6059 | 0.1320 | 0.1380 |
| | 36 | 13.73 | 53.5 | 10.1 | 180 | 0.1187 | 0.1355 | 0.5988 | 0.1470 |
| | 37 | -10.62 | 43 | 8.3 | 172 | 0.4802 | 0.5117 | 0.0080 | 0.0000 |
| | 38 | -4.43 | 45.6 | 8.8 | 176 | 0.6091 | 0.1306 | 0.1275 | 0.1329 |
| | 39 | -1.48 | 48.1 | 9.1 | 174 | 0.0065 | 0.9830 | 0.0063 | 0.0042 |
| | 40 | 9.58 | 52.7 | 9.9 | 177 | 0.0000 | 0.4974 | 0.4876 | 0.0150 |
| | 41 | 16.9 | 57.1 | 10.7 | 181 | 0.0037 | 0.4828 | 0.0083 | 0.5052 |
| | 42 | 10.15 | 51 | 9.7 | 179 | 0.2367 | 0.2498 | 0.2507 | 0.2628 |
| | 43 | 3.3 | 48.9 | 9.2 | 173 | 0.4580 | 0.0179 | 0.4971 | 0.0270 |
| | 44 | 17.34 | 59.55 | 10.8 | 175 | 0.0000 | 0.0000 | 0.9717 | 0.0283 |
| | 45 | 30.65 | | | | 0.0000 | 0.0000 | 0.0290 | 0.9710 |
| | 46 | 17.23 | 57 | 10.6 | 179 | 0.0000 | 0.0000 | 0.9710 | 0.0290 |
| | 47 | 13.92 | 51 | 9.7 | 179 | 0.4660 | 0.0000 | 0.0341 | 0.4999 |
| | 48 | 14.55 | 53.15 | 9.9 | 175 | 0.3102 | 0.0000 | 0.3317 | 0.3581 |

FIGURE 4

Table C. Examples 49-72

| | Example | Pour Point (°C) | Kinematic Viscosity | | | Fatty Acid Content | | | |
|---|---|---|---|---|---|---|---|---|---|
| | | | KV 40 | KV 100 | VI | C-12 | C-14 | C-16 | C-18 |
| PG-03 | 49 | 22.76 | 58.9 | 9.7 | 149 | 0.0000 | 0.3176 | 0.3300 | 0.3524 |
| | 50 | 9.06 | 49.1 | 8.2 | 140 | 0.0000 | 0.9813 | 0.0100 | 0.0087 |
| | 51 | -9.73 | 40.2 | 7 | 135 | 0.9215 | 0.0354 | 0.0141 | 0.0290 |
| | 52 | 7.32 | 49.1 | 8 | 133 | 0.3312 | 0.3325 | 0.3260 | 0.0104 |
| | 53 | 30.38 | | | | 0.0090 | 0.0088 | 0.4778 | 0.5044 |
| | 54 | 14.82 | 51.7 | 8.6 | 143 | 0.3318 | 0.3151 | 0.0197 | 0.3334 |
| | 55 | -11.43 | 39.9 | 7 | 137 | 0.9509 | 0.0254 | 0.0000 | 0.0237 |
| | 56 | 26.97 | 58.8 | 9.6 | 147 | 0.1701 | 0.1208 | 0.1209 | 0.5882 |
| | 57 | -2.16 | 43.4 | 7.5 | 140 | 0.5155 | 0.4845 | 0.0000 | 0.0000 |
| | 58 | 36.13 | | | | 0.0000 | 0.0000 | 0.0092 | 0.9908 |
| | 59 | 14.05 | 51.6 | 8.6 | 144 | 0.1145 | 0.5996 | 0.1262 | 0.1597 |
| | 60 | 20.55 | 56.8 | 9.5 | 151 | 0.1188 | 0.1362 | 0.6014 | 0.1436 |
| | 61 | -2.32 | 43.5 | 7.6 | 143 | 0.4962 | 0.5038 | 0.0000 | 0.0000 |
| | 62 | 3.39 | 45.7 | 7.8 | 140 | 0.5903 | 0.1382 | 0.1280 | 0.1435 |
| | 63 | 8.54 | 48.8 | 7.8 | 128 | 0.0241 | 0.9759 | 0.0000 | 0.0000 |
| | 64 | 16.76 | 53.5 | 9 | 149 | 0.0000 | 0.5021 | 0.4823 | 0.0156 |
| | 65 | 23.48 | 59.5 | 9.7 | 147 | 0.0080 | 0.4729 | 0.0130 | 0.5061 |
| | 66 | 16.74 | 53.9 | 8.9 | 144 | 0.2353 | 0.2625 | 0.2585 | 0.2436 |
| | 67 | 17.66 | 52.6 | 8.8 | 146 | 0.4946 | 0.0000 | 0.0000 | 0.5054 |
| | 68 | 24.68 | 61.3 | 9.8 | 144 | 0.0137 | 0.0000 | 0.9488 | 0.0375 |
| | 69 | 36.67 | | | | 0.0000 | 0.0000 | 0.0299 | 0.9701 |
| | 70 | 25.54 | 61.8 | 9.9 | 145 | 0.0000 | 0.0000 | 0.9520 | 0.0480 |
| | 71 | 18.76 | 52 | 8.8 | 148 | 0.4798 | 0.0000 | 0.0000 | 0.5202 |
| | 72 | 20.7 | 55.5 | 9.2 | 147 | 0.3210 | 0.0000 | 0.3304 | 0.3486 |

FIGURE 5

Table D. Examples 73-79

| Example | 73 | 74 | 75 | 76 | 77 | 78 | 79 | JD HyGard |
|---|---|---|---|---|---|---|---|---|
| PO # | 10 | 10 | 10 | 10 | 10 | 5 | 5 | N/A |
| Fatty Acid | HO Soybean | Soybean | Canola | Coconut | Lauric | Lauric | Oleic | N/A |
| Pour Point (°C) | -24 | -15 | -42 | -15 | -36 | -24 | -42 | -39 |
| Copper Strip Corrosion | 1B | 1B | 1B | 1B | 1B | 1B | 1A | 1A |
| KV 40 °C (cSt) | 68.35 | 59.36 | 65.34 | 58.02 | 55.76 | 38.66 | 54.22 | 58.71 |
| KV 100 °C (cSt) | 13.11 | 11.93 | 12.78 | 10.59 | 10.2 | 7.559 | 10.81 | 9.283 |
| Viscosity Index | 197 | 202 | 200 | 175 | 173 | 167 | 195 | 139 |
| 4 Ball Wear Scar (mm) | 0.204 | 0.56 | 0.21 | 0.494 | 0.482 | 0.519 | 0.652 | 0.192 |

FIGURE 9

Table E. Examples 80-84

| Example | Functional FA (%) | Pour Pt. (°C) | KV40 (cSt) | KV100 (cSt) | VI |
|---|---|---|---|---|---|
| 80 | 0 | -17.72 | 58.35 | 10.8 | 179 |
| 81 | 5 | -18.23 | 72.8 | 11.8 | 158 |
| 82 | 10 | -18.59 | 85.9 | 13.1 | 153 |
| 83 | 5 | -18.50 | 70.2 | 11.0 | 148 |
| 84 | 10 | -17.77 | 77.5 | 12.0 | 150 |

FIGURE 10

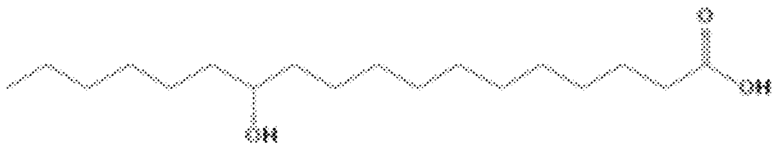
12-Hydroxysteric acid
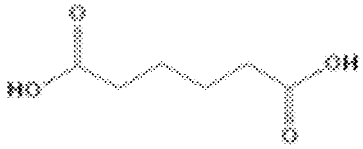
Adipic Acid
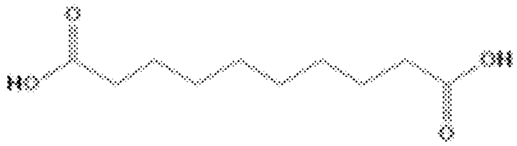
Sebacic Acid
FIGURE 11

Table F. Example 85

| Test | Envirotemp FR-3 | Envirotemp 200 | Example 85 |
|---|---|---|---|
| Dielectric BD Disk | 47 | 43 | 50 |
| Color | 0.5 | <1.0 | 0.5 |
| Interfacial Tension (25°C) | 27 | 29 | 24.9 |
| Flash Point (°C) | 330 | 270 | 303 |
| Fire Point (°C) | 360 | 306 | 324 |
| Pour Point (°C) | -21 | -50 | -42 |
| Specific gravity (15°C) | 0.92 | 0.97 | 0.94 |
| KV100 (cSt) | 8 | 5.6 | 10.8 |
| KV40 (cSt) | 33 | 29 | 54.2 |
| Visual examination | clear light green | bright and clear | clear |
| Acid Value (mg KOH/g) | 0.042 | 0.03 | 0.18 |
| Water Content (ppm) | 20 | 60 | 680 |

FIGURE 12

Table G. Examples 86-88

| Example | Pour Pt. (°C) | KV40 (cSt) | KV100 (cSt) | VI |
|---|---|---|---|---|
| 86 | -1.1 | 55.2 | 11.2 | 201 |
| 87 | 36.51 | N/A | N/A | N/A |
| 88 | -15.81 | 52.65 | 10.6 | 196.5 |

FIGURE 13

R = H, $CH_3$, $CH_2CH_3$ a) Glycerol ester b) Alkoxylated glycerol ester

Table 1. Compositions of Invention Examples

| Example | Polyol | Fatty Acid | Undercool (°C) | Melt Enthalpy (J/g) |
|---|---|---|---|---|
| 89 | Glycerol | C8-C10 | 29.16 | 94.61 |
| 90 | TMP | Saturate Blend | 16.94 | 72.97 |
| 91 | PG10 | C8-C10 | 6.97 | 10.24 |
| 92 | Glycerol | C12 | 28.56 | 188.80 |
| 93 | PG03 | C12 | 8.53 | 74.29 |
| 94 | PG10 | C12 | 7.79 | 45.73 |
| 95 | Glycerol | Pamolyn | 33.83 | 65.22 |
| 96 | PG03 | Pamolyn | 14.05 | 28.27 |
| 97 | PG05 | Pamolyn | 8.72 | 12.73 |
| 98 | PG10 | Pamolyn | 7.55 | 13.29 |
| 99 | PG10 | BFT | 10.22 | 16.85 |
| 100 | PG10 | Canola | 9.99 | 12.52 |
| 101 | PG10 | HOSO | 8.31 | 15.36 |
| 102 | PG10 | SBO | 8.77 | 18.61 |
| 103 | PG10 | Coconut | 11.4 | 28.29 |
| 104 | PG10 | Coconut/BFT | 10.48 | 26.91 |
| 105 | PG10 | Coconut+5% EH | 11.21 | 36.65 |
| 106 | PG10 | Coconut+5% C18 Iso | 13.09 | 35.28 |
| 107 | PG10 | C18 Iso | 8.72 | 13.79 |
| 108 | PG10 | BFT+33% 12-HSA | 19.86 | 16.87 |
| 109 | PG10 | BFT+16% Sebacic | 5.2 | 9.998 |
| C1 | Soybean Oil | | 26.77[A] | 65.03 |
| C2 | High Oleic Soybean Oil | | 44.39[B] | 72.68 |
| C3 | Canola Oil | | 39.63 | 61.85 |
| C4 | Coconut Oil | | 18.49 | 103.6 |
| C5 | TMP Trioleate | | 10.53 | 30.74 |

A: Undercool of high melting saturated components (minor fraction) is 4.78°C.
B: Undercool of high melting saturated components (minor fraction) is 18.42°C.

FIGURE 15

Table 2: 1H NMR Shifts [ppm] for Methylene and Methine Protons of Natural and Synthetic Ester Backbone

| Proton Label | Ex. 89 | Ex. 90 | Proton Label | Ex. 91 |
|---|---|---|---|---|
| alpha - Methylene | 4.19 | 3.99 | Glycerol Methylene | 3.38 |
| beta - Methine | 5.24 | - | Glycerol Methine | 5.01 |

FIGURE 16

Table 3: RPVOT Data for Neat and Formulated Base oils

| Example | RPVOT [min.] |
|---|---|
| Soybean Oil[1] | 17 |
| Canola Oil[1] | 14 |
| TMP Trioleate[2] | 13 |
| 98 | 28 |
| 103 | 31 |

1. Data sourced from King Industries product literature
2. Data sourced from Lubrication Science, 2015, 27(6), p369

FIGURE 17

Table 4: Hydrolytic Stability (ASTM D2619) Data for Saturated Ester Base Oils

| Example | 92 | 103 | 91 | 90 |
|---|---|---|---|---|
| Weight Change of Cu Panel ($mg/cm^2$) | -0.175 | -0.017 | -0.025 | -0.183 |
| Appearance of Cu Panel | 1b (Shiny) | 1b-2a (Shiny) | 1b (Shiny*) | 1b (Shiny) |
| Total AV of $H_2O$ Layer (mg KOH/g) | 3.3 | 0.47 | 0.76 | 6.5 |

* w/ some dark grey

FIGURE 18

Table 5: Thermodynamic Data for C12 Esters Analyzed by Differential Scanning Calorimetry

| Example | Solid Onset (°C) | Complete Melt (°C) | Undercool (°C) | Solids% @ Onset +5C | Solids% @ Onset +10C | Melt Enthalpy (J/g) |
|---|---|---|---|---|---|---|
| 92 | 21.72 | 50.28 | 28.56 | 100.00 | 100.00 | 188.80 |
| 93 | -14.97 | -6.44 | 8.53 | 31.04 | 2.85 | 74.29 |
| 94 | -40.7 | -32.91 | 7.79 | 18.06 | 3.59 | 45.73 |
| 90 | -4.4 | 12.54 | 16.94 | 81.39 | 46.39 | 72.97 |

FIGURE 19

Table 6: Undercool and Melt Enthalpy of Analogous Glycerol, TMP, and Propoxylated Glycerol Esters

| Example | Polyol | Fatty Acid | Undercool (°C) | Melt Enthalpy (J/g) |
|---|---|---|---|---|
| 89 | Glycerol | C8-C10 | 29.16 | 94.61 |
| 91 | PG10 | | 6.97 | 10.24 |
| C4 | Glycerol | Coconut | 18.49 | 103.6 |
| 90 | TMP | | 16.94 | 72.97 |
| 103 | PG10 | | 11.4 | 28.29 |
| 95 | Glycerol | Oleic | 33.83 | 65.22 |
| C5 | TMP | | 10.53 | 30.74 |
| 98 | PG10 | | 7.55 | 13.29 |
| C1 | Glycerol | Soy | 26.77[A] | 65.03 |
| 102 | PG10 | | 8.77 | 18.61 |
| C2 | Glycerol | High Oleic Soy | 44.39[B] | 72.68 |
| 101 | PG10 | | 8.31 | 15.36 |
| C3 | Glycerol | Canola | 39.63 | 61.85 |
| 100 | PG10 | | 9.99 | 12.52 |

A: Undercool of high melting saturated components (minor fraction) is 4.78°C.
B: Undercool of high melting saturated components (minor fraction) is 18.42°C.

FIGURE 20

Table 7: Cold Temperature Behavior of Various Esters

| Example | Cloud Point [°C] | Pour Point [°C] | Melt Enthalpy (J/g) | KV 40 (cSt) | KV 100 (cSt) | VI | Transparency |
|---|---|---|---|---|---|---|---|
| 95 | -22 | -18 | 65.22 | 41.83 | 9.08 | 207 | Opaque |
| 96 | -28 | -22.5 | 28.27 | 47.85 | 10 | 202 | Opaque |
| 97 | -32 | -34.5 | 12.73 | 54.77 | 11.04 | 199 | Translucent |
| 98 | - | -30 | 13.29 | 69.06 | 13.76 | 207 | Transparent |
| Additional Transparent Esters | | | | | | | |
| 91 | - | -40 | 10.24 | 44.36 | 8.77 | 182 | Transparent |
| 100 | - | -43.5 | 12.52 | 65.34 | 12.78 | 200 | Transparent |
| 107 | - | -45 | 13.79 | 115.18 | 17.63 | 169 | Transparent |
| 109 | - | -33 | 9.998 | 161.64 | 26.61 | 202 | Transparent |

FIGURE 21

Table 8: PG10-Whole Cut Fatty Acid Esters

| Example | Cloud Point [°C] | Pour Point [°C] | KV 40 (cSt) | KV 100 (cSt) | VI |
|---|---|---|---|---|---|
| 98 | - | -30 | 69.06 | 13.76 | 207 |
| 99 | -35 | -37.5 | 68.53 | 13.44 | 203 |
| 100 | - | -43.5 | 65.34 | 12.78 | 200 |
| 101 | -31 | -30 | 68.35 | 13.11 | 197 |
| 102 | -19 | -22.5 | 59.36 | 11.93 | 202 |
| 103 | -20 | -27 | 55.75 | 10.58 | 183 |
| 91 | - | -40 | 44.36 | 8.77 | 182 |
| 104 | -35 | -37.5 | 68.53 | 13.44 | 203 |

FIGURE 22

Table 9: Biodegradation Data for Example 103

| Time (days) | Mean Degradation (%) |
|---|---|
| 0 | 0 |
| 1 | 3 |
| 4 | 19 |
| 7 | 47 |
| 11 | 60 |
| 14 | 62 |
| 18 | 71 |
| 21 | 67 |
| 25 | 74 |
| 27 | 73 |
| 28 | 73 |

FIGURE 23

Table 10: Biobased Carbon Analysis for Example 98 & 103

| Sample | 14C (Meas.) (pMC) | SD | δ13C (o/oo VPDB) | 14C (Corr.) (pMC) | % Biobased Carbon | SD |
|---|---|---|---|---|---|---|
| Ex. 98 | 66.43 | 0.23 | -24.66 | 66.38 | 66 | 1 |
| Ex. 103 | 56.65 | 0.22 | -29 | 57.11 | 57 | 1 |

FIGURE 24

Table 11: PG10 Branched, Functional, and Diacid Esters

| Example | Cloud Point [°C] | Pour Point [°C] | KV 40 (cSt) | KV 100 (cSt) | VI |
|---|---|---|---|---|---|
| 105 | -12 | -31.5 | 57.94 | 11.07 | 187 |
| 106 | -14 | -31.5 | 61.34 | 11.57 | 187 |
| 107 | - | -45 | 115.18 | 17.63 | 169 |
| 108 | -38 | -36 | 109.36 | 18.88 | 194 |
| 109 | - | -33 | 161.64 | 26.61 | 202 |

FIGURE 25

Table 12: Formulated Oil Performance Comparison

| | | Ex. 103 Turbine | Ex. 103 Hydraulic | C1 | C3 | Chevron GST |
|---|---|---|---|---|---|---|
| Copper Corrosion | ASTM D130 | 1a | 1b | 1a | 1b | 1a |
| 4-Ball Wear | ASTM D4172 | 0.49 mm | 0.48 mm | 0.50 mm | 0.52 mm | 0.50 mm |
| RPVOT | ASTM D2272 | 1010 min. | 910 min. | 268 min. | 102 min. | 1240 min. |
| 4-Ball Weld | ASTM D2783 | 160 | - | - | - | 126 |
| Coefficient of Friction | ASTM D6425 | 0.072 | - | - | - | 0.072 |
| Oxidation Onset (°C) | ASTM E2009-08 | 258 | - | - | - | 249 |

FIGURE 26

Table 13: Ethoxylated glycerol esters properties

| Example | Func. Glycerol | Fatty Acid | Pour Point (°C) | KV40 (cSt) | KV100 (cSt) | VI |
|---|---|---|---|---|---|---|
| 110 | EG12 | Coconut | -3 | 55.2 | 11.2 | 201 |
| 103 | PG10 | Coconut | -27 | 55.75 | 10.58 | 183 |
| 111 | EG12 | Lauric | -16.5 | 52.6 | 10.6 | 197 |
| 94 | PG10 | Lauric | -37.5 | 56.37 | 10.79 | 187 |
| 98 | PG10 | Oleic | -39 | 69.06 | 13.76 | 207 |
| 112 | PG10EGc | Oleic | -45 | 70.86 | 13.46 | 196 |

FIGURE 27

BIODEGRADABLE LUBRICANT WITH TAILORED HYDROLYTIC STABILITY AND IMPROVED THERMAL STABILITY THROUGH ALKOXYLATION OF GLYCEROL

TECHNICAL FIELD

The subject matter disclosed herein is generally directed to methods of stabilizing the beta hydrogen adjacent to the ester bond(s) of a glycerol derivative by insertion of alkoxy groups to significantly improve the hydrolytic and thermal stability of the ester bonds, and it allows for control of the molar density of ester bonds in the lubricant to maximize hydrolytic stability while maintaining biodegradability and further improving performance properties.

BACKGROUND

The current state of the art [Rudnick, L. R. (ed.). (2020). Synthetics, Mineral Oils, and Bio-Based Lubricants (pp. 60, 131, 419). CRC Press] considers natural esters (triglyceride oils) to be inferior base oils for use in industrial lubricants despite their outstanding lubricity, high viscosity indices, and high flash and fire points while exhibiting a high level of bio content and biodegradability. In patent application WO 03/062355 A1, the disclosure states that compared to glycerol, trimethylolpropane, pentaerythritol, and neopentyl glycol "are preferred as they have improved thermal stability because of the absence of a hydrogen atom in the beta position with respect to the OH groups, the presence of which would involve a risk of dehydration at elevated temperatures." (Emphasis added.)

Various lubricants have been disclosed. For example, U.S. Pat. No. 3,337,595 discloses the making of fatty acid esters of propoxylated glycerol for use as defoaming aids. The preferred embodiment of the art is diesters of propoxylated glycerol and blends of said diesters with fatty acid methyl esters and esters of polyethylene glycol.

U.S. Pat. No. 3,530,070 discloses the use of propoxylated polyols as synthetic lubricants. The compositional space encompasses multiple polyols (trimethylol propane, neopentyl glycol, pentaerythritol, dipentaerythritol, sorbitol, and glycerol) propoxylated up to an average of 72 PO units per mole of polyol and esterified to various fatty acids (≤C12). This patent space encompasses materials that are low in biocontent (<40%) or low in biodegradation.

U.S. Pat. No. 4,031,118 is concerned with ester containing processes and compositions as detergents and dispersants in fuels and lubricants. The compositions disclosed are high MW (1000-10000 g/mol) polyether polyols (EO/PO copolymers) esterified with very long chain (≥C30) fatty acids. This patent space encompasses materials with low to negligible biobased carbon content and low biodegradability.

U.S. Pat. No. 5,916,854 discloses the use and composition of interesterified and alkoxylated lubricating oils. The compositions are product by process entailing the interesterification of natural oils with glycerol or free fatty acids with simultaneous alkoxylation. The resultant products are a blend of many different compositions including monoesters, diesters, and linear esters.

PCT WO1995002659 discloses lubricating oil compositions for use as hydraulic fluids. Two processes are used to generate the claimed compositions:

Propoxylation of glycerol to an average of <3 PO units per glycerol with preferred embodiments of 1 PO unit per glycerol followed by esterification with FA from C6-C24.

One pot process like that listed under U.S. Pat. No. 5,916,854 creating product by process.

PCT WO2012134792 discloses a lubricant composition comprising polymers of glycerol that have been propoxylated to an average of 6-15 PO units followed by esterification with FA from C8-C15. Preferred claims are alkoxylates (PO 8-12) and FA esters (C9-11) of diglycerol and triglycerol.

PCT WO2014124698 concerns the composition and use of pentaerythritol derived ester lubricants. The preferred composition claimed and described consists of pentaerythritol with an average degree of propoxylation of 5 subsequently esterified with C8/C10 fatty acids or oleic acid.

Tetramer Technologies' patent application US2019/0367831 A1 discloses the use of esterified propoxylated polyols with long chain fatty acids (≥C14) to produce base oils with viscosities and pour points corresponding to those of mineral base oils.

High-temperature oxidative stability of a lubricant molecule depends heavily on the amount and configuration of hydrogen on the beta-carbons to an ester. Additionally, natural esters that have pour points suitable for industrial lubricants contain significant unsaturation and are prone to oxidative breakdown leading to the formation of varnish and, in some cases, gelation of the oil, which reduces flow and can potentially lead to mechanical failure. Partially and fully saturated natural esters, while oxidatively stable, have poor cold temperature properties and are prone to crystallization. Because of these limitations, natural esters are only used in applications such as total loss lubricants for environmentally sensitive areas.

While synthetic neopentyl polyol esters are designed for high thermo-oxidative and hydrolytic stability, it is understood by those skilled in the art that hydrolytic stability and biodegradability are closely related because the first step of biodegradation is the hydrolysis of the ester. As such, materials designed for high levels of hydrolytic performance are not necessarily suitable as an environmentally acceptable lubricant, and more so, may be poorly designed for biodegradation [Totten, G. E., Westbrook, S. R., Shah, R. J., (ed.). (2003). Fuels and Lubricants Handbook: Technology, Properties, Performance, and Testing (pp. 274). ASTM International].

Environmentally Acceptable Lubricants (EAL) are a new class of lubricants which can have varied definitions depending on country, industry, and application. However, it is generally agreed on that an EAL should have good biodegradability, low bioaccumulation, and low toxicity. While not always a requirement, it is generally preferred that the EAL has a high level of biobased carbon content in order to minimize the environmental impact of the oil production. As governments and non-governmental organizations begin to regulate and legislate the use of EALs, uniform standards are beginning to emerge. The European EcoLabel uses a definition which requires a lubricant to be non-toxic, non-bioaccumulating, and biodegradable (>60% biodegradation according to the OECD 301B). If a lubricant is labeled "bio-based" or "bio-lubricant", it must possess biobased carbon content of greater than 25% according to Commission Decision (EU) 2018/1702.

What is needed in the art are modification and composition(s) of glycerol esters lubricants wherein the molecule possesses a high level of biocontent and optimized hydrolytic stability to maximize performance while still passing biodegradation testing. Further, this modification and composition(s) of glycerol esters should enhance oxidative and thermal stability while improving cold weather performance.

Citation or identification of any document in this application is not an admission that such a document is available as prior art to the present disclosure.

SUMMARY

In certain example embodiments, a synthetic ester lubricating base oil is provided. The base oil may include an ester of an alkoxylated glycerol with an average degree of alkoxylation ≥3, and at least one fatty acid having ≥8 carbon atoms. The synthetic lubricating base oil exhibits, as compared to a glycerol ester with same fatty acid composition: increased oxidative, thermal and hydrolytic stability, decreased melting enthalpy, and decreased undercooling and has a single crystal melt point or an amorphous phase for each fraction of the synthetic lubricating base oil. Further, thermal oxidative stability of the synthetic ester lubricating base oil may be increased by greater than 25%, more preferable greater than 40%, and more preferably by greater than 60%, as determined by Rotating Pressure Vessel Oxidation Test (RPVOT) lifetime, compared to a glycerol ester of the same fatty acid composition. Additionally, hydrolytic stability of the base oil may be improved as measured by the reduction of the total acid value number by greater than 50%, more preferable greater than 60%, and more preferably greater than 70%. Further, melting enthalpy may be decreased relative to a glycerol ester with same fatty acid composition by over 50%, more preferable 60%, more preferably 70%, and even more preferably 80%. Again, melting enthalpy may be decreased such that the lubricant does not exhibit a detectable cloud point and maintains transparency. Yet still, undercooling may be decreased by greater than 30%, preferably greater than 50%, more preferably greater than 70% decrease, and even more preferably greater than 75%. Still yet, the alkoxylate may be derived from ethylene oxide (EO), propylene oxide (PO), butylene oxide (BO), or a combination thereof. Further again, the alkoxylated glycerol may preferably have a range from 3 to 20 propoxy groups per molecule, more preferable a range of 5 to 12, more preferable yet is a range of 8 to 11, and even more preferable is a degree of propoxylation of 10. Yet further, at least one fatty acid may be a dicarboxylic acid. Still yet, the dicarboxylic acid may comprise oxalic acid, malonic acid, succinic acid, glutaric acid, adipic acid, pimelic acid, suberic acid, azelaic acid, sebacic acid, undecanedioic acid, dodecanedioic acid, octadecanedioic acid or combinations of the above. Yet again, at least one fatty acid may be a functionalized acid. Again still, the functionalized acid may comprise 12-hydroxystearic acid. Still again, functionalization may comprise epoxidation, maleination, metathesis, amidation, halogenation, hydration, hydrogenation, estolide formation, hydroformylation, dimerization, or vulcanization of the synthetic ester. Moreover, at least one fatty acid may be branched. Still further, the branched acid may comprise 2-ethylhexanoic acid or isostearic acid. Yet again, the lubricating base oil may not be less than 40 percent biodegradable in the 10-day window of OECD 301B test. Again, the lubricating base oil may be at least 25 percent biobased carbon. Again yet, the disclosure provides a synthetic lubricant including the synthetic ester lubricating base oil that may incorporate at least one additive selected from an antioxidant, an anti-wear agent, an anticorrosion agent, an anti-sludge agent, an anti-foam agent, a demulsifier, a viscosity index improver agent, a detergent/dispersant, a pour-point depressant, an alkalinity improver, a friction modifier, a seal swell agent, a metal deactivator/complexing agent, and/or an extreme pressure agent. Still yet, thermal oxidative stability, as determined by RPOVT lifetime, may be greater than 600 minutes, more preferably greater than 800 minutes, and even more preferably greater than 1000 minutes.

In a further embodiment, the current disclosure provides the synthetic ester lubricating base oil as a hydrolytically stable, biodegradable lubricant. Further, the alkoxylated glycerol ester possesses hydrolytic stability and biodegradation by tailoring ester bond stability and ester density through use of alkoxylation wherein degradation products of the alkoxylated glycerol ester are nontoxic. ISO viscosity grades of the lubricant may be from 32-150, more preferably 46-100, and even more preferably 46-68.

The current disclosure also provides a method of stabilizing beta-hydrogen of a glycerol ester and diluting molar density of the esters bond in an ester base oil wherein hydroxyl groups of the glycerol are alkoxylated with ethylene oxide, propylene oxide, butylene oxide, or a combination thereof, to form an alkoxylated glycerol ester with thermal, oxidative, and hydrolytic stability.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which:

FIG. 3 shows Table A: Base oil property data for examples 1-24.

FIG. 4 shows Table B: Base oil property data for examples 25-48.

FIG. 5 shows Table C: Base oil property data for examples 49-72.

FIG. 9 shows Table D: Lubricant specific data comparison for examples 73-79 and John Deere HyGard Transmission and Hydraulic OIL.

FIG. 10 shows Table E: Base oil properties for modified base oil examples 80-84.

FIG. 11 shows molecular diagrams for adipic, sebacic, and 12-hydroxystearic acids.

FIG. 12 shows Table F: Dielectric fluid test data comparison for example 85 and two commercial biodegradable dielectric fluids.

FIG. 13 shows Table G: Base oil data for esterified ethoxylated glycerol samples with coconut, stearic, lauric acids.

FIG. 15 shows Table 1: Compositions of Disclosure Examples.

FIG. 16 shows Table 2: 1H NMR Shifts for Methylene and Methine Protons of Natural and Synthetic Ester Backbone.

FIG. 17 shows Table 3: RPVOT Data for Neat and Formulated Base Oils.

FIG. 18 shows Table 4: Hydrolytic Stability (ASTM D2619) Data for Saturated Ester Base Oils.

FIG. 19 shows Table 5: Thermodynamic Data for C12 Esters Analyzed by Differential Scanning Calorimetry.

FIG. 20 shows Table 6: Undercool and Melt Enthalpy of Analogous Glycerol, TMP, and Propoxylated Glycerol Esters.

FIG. 21 shows Table 7: Cold Temperature Behavior of Various Esters.

FIG. 22 shows Table 8: PG10-Whole Cut Fatty Acid Esters.

FIG. 23 shows Table 9: Biodegradation According to OECD-301B.

FIG. 24 shows Table 10: Percent Biobased Carbon (ASTM Method D6866-20).

FIG. 25 shows Table 11: PG10 Branched, Functional, and Diacid Esters.

FIG. 26 shows Table 12: Formulated Oil Performance Comparison.

FIG. 27 shows Table 13: Examples of Ethoxylated Glycerol Esters.

Figure 1:
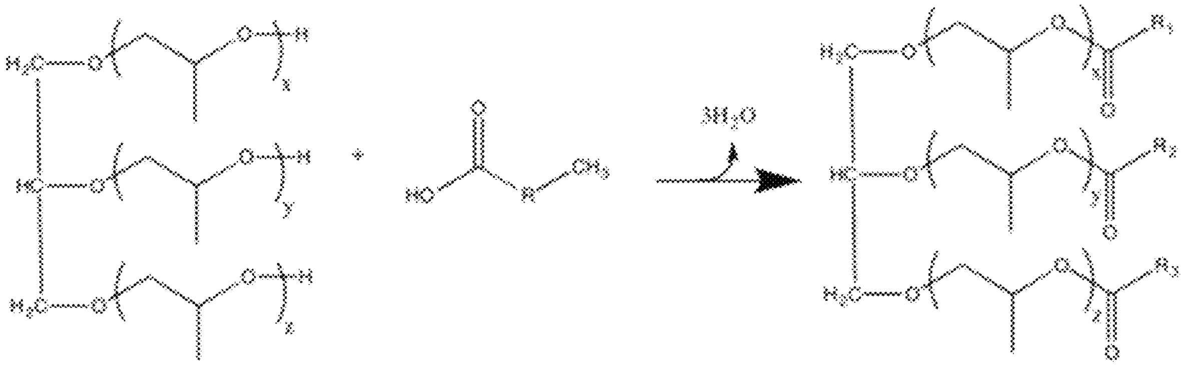
FIG. 1 shows Scheme A: Reaction scheme for the synthesis of esterified propoxylated glycerol from the propoxylated glycerol and fatty acids base components.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 0.5% to about 2.4%; about 0.5% to about 3.2%, and about 0.5% to about 4.4%, and other possible sub-ranges) within the indicated range.

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosed disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The term "optional" or "optionally" means that the subsequent described event, circumstance or substituent may or may not occur, and that the description includes instances where the event or circumstance occurs and instances where it does not.

The term "molecular weight", as used herein, can generally refer to the mass or average mass of a mole of a material. A mole is a defined number of molecules (Avogadro constant). If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values of the specified components in the disclosed composition or formulation are equal to 100.

As used herein, the terms ester refers to a type of chemical bond or, alternatively, to a type of molecule which is composed of ester bonds. When referring to a class of molecule, as in "alkoxylated glycerol ester," "propoxylated glycerol ester," "glycerol ester," "TMP ester," and "synthetic ester," it should be understood that the fully esterified ester variants of the molecule are being described. In oil chemistry it is not unusual to have a monoacylglyceride or diacylglyceride which are esters but are not equivalent to a triacylglyceride. When describing a glycerol ester or alkoxy ester, the fully esterified molecule is being described. A fully esterified ester is understood to be when a hydroxyl value of less than 15 mg KOH/g is achieved, or more preferably less than 10 mg KOH/g, or most preferably less than 5 mg KOH/g.

When referring to alkoxylated materials, it should be understood that EO, PO, and BO may be used to describe the alkylene oxide reactants, ethylene oxide, propylene oxide, and butylene oxide, respectively, or EO, PO, and BO may be used to describe the polyether composition, ethoxy, propoxy, and butoxy, respectively, of the alkoxylated glycerol. Further, propoxylating and oxypropylating are used synonymously, as well propoxylated and oxypropoxylated. Likewise, ethoxylating and oxyethylating are used synonymously, as well ethoxylated and oxyethylated.

Figure 14:
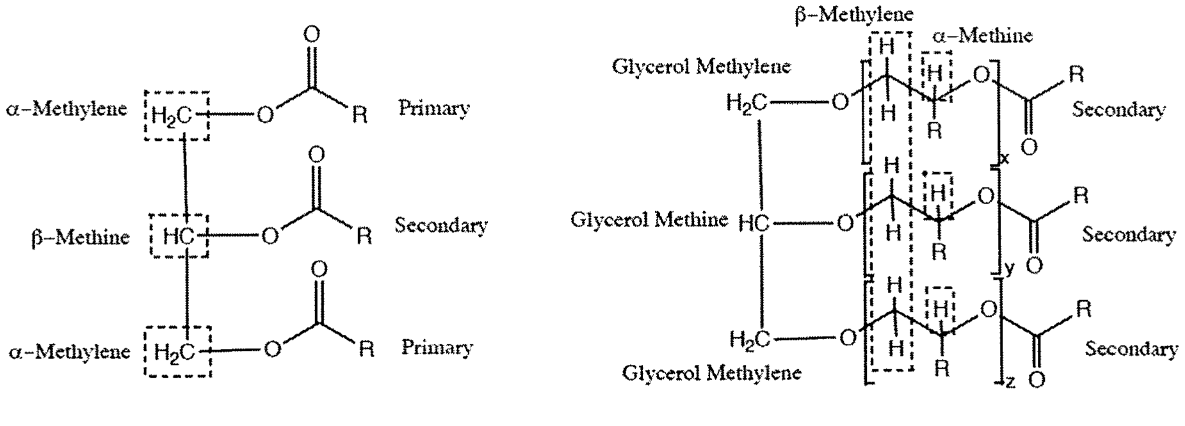
FIG. 14 shows a schematic representation of glycerol (left) and alkoxylated glycerol (right) esters, highlighting the α and β hydrogens of each species and the primary and secondary alcohols.

The term "degree of alkoxylation" herein should be taken to mean the average number of alkylene oxide molecules (EO, PO, and/or BO) that have been attached to a given polyol molecule. When describing the degree of alkoxylation, the sum of x+y+z as seen in FIG. 14 at B is the degree of alkoxylation, where x, y, and z are integers. Further, the degree of alkoxylation can be the average degree of alkoxylation for all molecules such that the degree of alkoxylation can be an integer or a fraction. In U.S. Pat. No. 6,495,188 B2 it is found that a stoichiometric ratio degree of alkoxylation, e.g. 3 PO per glycerol, results in approximately 63% of the glycerol hydroxyl groups being reacted. A degree of alkoxylation of 4 resulted in 82% of free glycerol hydroxyl groups being alkoxylated, and a degree of alkoxylation of 5 resulted in complete alkoxylation.

"Insertion" as used herein should be taken to mean putting the alkoxy groups in the molecular structure but not to mean insertion in the chemistry sense of a reaction mechanism.

The lubricating base oils of the present disclosure combine the lubricity and wear resistance of vegetable oils, the low temperature pour points of synthetic esters, and the range of viscosities of the "synthetic" petroleum derivatives, while being lower cost than both current synthetic esters and Group III+/PAO lubricants.

By utilizing long chain fatty acid(s) in conjunction with alkoxylated polyol(s), this disclosure generates base oils that have high bio-based content (>60 wt. %, such as >65, >70, >75, >80, >85, >90, >95, etc.), and high biodegradability. Bio-based content refers to materials which are derived from biological products or renewable domestic agricultural materials (including plant, animal, and marine materials) or forestry materials or an intermediate feedstock. Biodegradability refers to the ability of a material to be decomposed by bacteria or other living organisms.

The above objectives are accomplished according to the present disclosure by providing in a first embodiment, a lubricating base oil. The lubricating base oil may include an alkoxylated polyol combined with at least one saturated fatty acid source to form an esterified alkoxylated polyol. Further, the esterified alkoxylated polyol comprises esterified propoxylated glycerol (EPG). Still further, the lubricating base oil is at least 40 percent biodegradable, such as for purposes of example only and not intended to be limiting 45 percent, 50, 55, 60, 65, 70, 75, 80, 85, 90, 95, etc., more preferably the lubricating base oil is at least 50 percent biodegradable, and most preferably the lubricating base oil is at least 60 percent biodegradable. Yet further, the base oil has an average degree of alkoxylation of greater than or equal to 3, such as 4, 5, 6, 7, 8, 9, 10 or greater. Further still, at least one fatty acid source comprising the oil is substantially long-chain (>C14, such as C15, C16, C17, C18, C19, C20, C21, C22, C23, C24, C25, C26, C27, C28, C29, C30, or longer) fatty acids. Even further, at least one fatty acid source comprising the oil is substantially unsaturated fatty acid. Even still further, the oil has a pour point at or below 0° C., and more preferably below −10° C., such as −15, −20, −25, −30, −35, −40, etc. Further yet, at least one fatty acid source may substantially be whole cut. Whole cut fatty acids are products of the direct fat splitting of natural oils and substantially comprise the native fatty acid composition of a representative natural oil. For the purposes of this disclosure, the whole cut fatty acid may be "cleaned" as understood by those of skill in the art and/or partially fractionated. Further, specific cuts, such as for purpose of example only but not intended to be limiting, high melt point cuts, may also be employed. Suitable whole cut fatty acids may be derived from vegetable or seed oils such as coconut oil, palm oil, palm kernel oil, palm fatty acid distillate soybean oil, rapeseed oil, canola oil, high oleic soybean oil, sunflower oil, corn oil, cottonseed oil, castor oil, olive oil, safflower oil, or linseed oil. Whole cut fatty acids may also be derived from animal oils such as fish oil, lard, tallow, or whale oil. Even further, the oil may include multifunctional fatty acids which may consist of dicarboxylic acids, hydroxy functional acids, or acids modified by techniques that may include but are not limited to epoxidation, maleination, metathesis, amidation, halogenation, hydration, or estolide formation.

In a further embodiment, a method is provided for forming a lubricating base oil. The method includes alkoxylating a polyol backbone and esterifying the alkoxylated polyol backbone with a saturated fatty acid, unsaturated fatty acid, or both to produce an esterified alkoxylated polyol. Further, the alkoxylated polyol comprises esterified propoxylated glycerol. Still further, the lubricating base oil is at least 60 percent biodegradable and may be 65, 70, 75, 80, 85, 90, or 95 percent or higher. Further yet, the base oil has an average degree of alkoxylation of equal to or greater than 3, such as 5, 7, etc. Still yet further, that at least one saturated fatty acid is equal to or greater than C12 saturated fatty acids, such as C13, C14, C15, C16, C17, C18, or higher. Even further, the saturated fatty acid is equal to or greater than C14, such as C15, C16, C17, C18, C19, C20, C22, C23, C24, C25, or higher. Yet still, the oil has a pour point of at or below −10° C., such as −15, −20, −25, −30, −35, −40, etc. Further yet, changing the feed ratio of at least one saturated fatty acid allows for tailoring properties of the lubricating base oil. Still further, that at least one saturated fatty acid source is whole cut. Still even further, at least one dicarboxylic acid is added as the esterified propoxylated polyol is formed. Yet still, that at least one saturated fatty acid comprises 12-hydroxystearic acid.

Some embodiments described herein are related to the synthesis and use of fatty acid esters of polyol alkoxylates, which possess viscosities characteristic of lubricating oils, have viscosity indices greater than 140, such as 145, 150, 155, 160, 165, 170, 175, 180, 185, 190, 195, 200, or higher, have pour points ≤0° C., such as −5, −10, −15, −20, −25, −30, −35, −40, etc. and are bio-based, biodegradable, and non-bioaccumulating alternatives to petroleum derived lubricating oils. A more preferred embodiment would consist of fatty acid esters of polyol alkoxylates with viscosity indices greater than 160, pour points ≤−10° C., bio-based content greater than 50%, and biodegradability greater than 40%, such as 45, 50, 55, 60, 65, 70, 75, 80, 85, 90, 95, or higher. Even further a more preferred embodiment would consist of fatty acid esters of polyol alkoxylates with viscosity indices greater than 180, pour points ≤−10° C., bio-based content greater than 55%, and biodegradability greater than 60%.

The polyol component of the present disclosure may be one or multiple common polyol substances such as, neopentyl glycol, trimethylol propane, glycerol, pentaerythritol, sorbitol, dipentaerythritol, or polyglycerols. The preferred polyol of this embodiment is glycerol.

The alkylene oxide component used to generate the polyol alkoxylate (polyether polyol) may consist of one or multiple alkylene oxides such as: ethylene oxide, propylene oxide, or butylene oxide. The alkoxylated polyol may contain ≥3 substituent alkoxy groups per polyol molecule. The preferred alkylene oxide of this embodiment is propylene oxide. The preferred degree of alkoxylation is ≥3 alkoxy groups per glycerol molecule, more preferably ≥5 alkoxy groups per glycerol molecule, and most preferably ≥10 alkoxy groups per glycerol molecule.

The fatty acid component of the esterified alkoxylated polyol may consist of saturated, unsaturated, or a combination of both saturated and unsaturated monobasic fatty acids with chain lengths of 4-24 carbons. The fatty acid component may also consist of saturated, unsaturated, or a combination therein of dibasic fatty acids with chain lengths ≥6 carbons. The fatty acid component may also consist of saturated, unsaturated, or a combination therein of hydroxy fatty acids. The fatty acid component may also consist of saturated, unsaturated, or a combination therein of branched fatty acids. The preferred fatty acids of this embodiment are both saturated and unsaturated monobasic fatty acids with chain lengths of 8-18 carbons.

The alkoxylated polyol may be synthesized utilizing common techniques known to those skilled in the art or may be acquired given a suitable commercially available source. The fatty acids may be derived from natural oils utilizing common techniques known to those skilled in the art or may be acquired from a suitable commercially available source. The esterification of the fatty acids and the alkoxylated polyol may be conducted with or without a catalyst utilizing techniques known to those skilled in the art. Non-catalyzed esterification may require the addition of molar excesses of fatty acid to the reaction mixture, reaction temperatures exceeding 150° C., application of vacuum to remove water, or a combination of said reaction parameters. Catalyzed esterification may be conducted at stoichiometric ratios of fatty acid to alcoholic hydroxyl, at temperatures below or above 150° C., at ambient pressure, or a combination of said reaction parameters. Suitable catalysts for the esterification of the alkoxylated polyol may include but are not limited to Iron (II) chloride, Titanium (IV) oxyacetylacetonate, Silica chloride, Graphene oxide, Sulfuric acid, Methanesulfonic acid, p-Tolunesulfonic acid, or Scandium (III) Triflate.

For the purposes of this embodiment the alkoxylated polyol was acquired from commercial sources and consisted of propoxylated glycerol with an average of 10 alkoxy groups per glycerol. The product is commonly supplied as 700 molecular weight glycerol-initiated polyether polyol (BASF: Pluracol GP730, Dow: Voranol 2070, Monument: Poly-G 30-240, Carpenter, Carpol GP700). For the purposes of this embodiment pure fatty acids utilized were selected from lauric (C12), myristic (C14), palmitic (C16), stearic (C18 sat.), and oleic (C18 unsat.). For the purposes of this embodiment whole cut fatty acids were also utilized and consist of coconut fatty acids, hydrogenated coconut fatty acids, soy fatty acids, canola fatty acids, and high oleic soy fatty acids.

The esterified propoxylated glycerol lubricant base oils of the present disclosure were prepared by charging an appropriate reaction vessel with the propoxylated glycerol and a 10% molar excess of the required fatty acid(s). The esterification was carried out at 240-250° C. and run under vacuum until the acid value of the reaction mixture was below about 15 mg KOH/g and the hydroxyl value of the reaction mixture was below about 20 mg KOH/g. Excess fatty acid and volatile reaction by products were then removed via short path distillation under vacuum and elevated temperature. Common ester purification techniques may be utilized in the absence of short path distillation. The ester product of the reaction was purified to an acid value <1 mg KOH/g with a preferred acid value <0.5 mg KOH/g, and a hydroxyl value <10 mg KOH/g with a preferred hydroxyl value <5 mg KOH/g.

The structure of the esterified propoxylated glycerol lubricating oil can be seen in Scheme A, see FIG. 1, which shows esterification of propoxylated glycerol (x+y+z=average degree of propoxylation) with fatty acid. One aspect of the present disclosure is that the polyether segments separating the glycerol (polyol) backbone and fatty acid chains characteristic of natural oils (synthetic esters) provide increased flexibility in the molecule enabling significant reductions in pour point compared to a natural oil or synthetic esters with an identical fatty acid profile. This lability in the molecule facilitates the use of higher fatty acids while maintaining the low pour points observed for esterified propoxylated glycerol lubricating oils. Another aspect of the present disclosure is that introduction of the polyether segments provides increased thermal and oxidative stability for the esterified propoxylated glycerol lubricants when compared to natural oils and non-neopentyl synthetic esters. A further aspect of the present disclosure is the use of long chain fatty acids to increase load carrying capacity of the lubricating base oil when compared to mid-chain fatty acid (C8-C11) synthetic esters. An additional aspect of the disclosure is an increase in detergency owing to the polyether segments of the base oil molecule as compared to common synthetic esters.

One aspect of the present disclosure is the functionalization of the fatty acid functionality of the esterified propoxylated glycerol lubricating base oil. Common techniques, known to those skilled in the art, may be used to modify the fatty acid chains to impart desired performance characteristics which may include epoxidation, maleination, metathesis, amidation, halogenation, hydration, estolide formation, or vulcanization.

One aspect of the present disclosure is the use of the esterified propoxylated glycerol as a lubricating base oil, either neat or as a formulated product, in Industrial Lubricants: gear oils, R&O compressor oils, R&O turbine oils; Automotive Oils: crankcase oils, transmission oils, gear oils; Metalworking Fluids; Marine Lubricants; Grease; Process Oils, or Dielectric Fluids.

A further aspect of the present disclosure is the use of esterified propoxylated glycerol base oils as biodegradable dielectric fluid. Dielectric fluids are used to cool, insulate and protect the internals of electronic devices. Typically, these fluids are used in transformers, capacitors, switches, etc. When used in a transformer, for example, dielectric fluids transport heat from the windings and core of the transformer or connected circuits to cooling surfaces.

Lubricants generally consist of liquid base oil and additives, whereas grease is a solid to semi-solid product consisting of lubricating oil (base oil) and thickener, unlike other lubricants. According to the ASTM (American Society for Testing and Materials), lubricating grease is a solid or semi-fluid substance containing a thickener agent and a lubricating liquid. In grease, the consistency of the product can be varied by thickening agents such as soap (calcium, lithium, and sodium), complex soap (calcium, lithium, lithium-calcium, aluminum), and bentone- or polyurea-based soap. The manufacturing of grease is a complex process involving various chemical reactions produced by different components. Grease are used as an alternative to liquid lubricants where space is restricted as well as to avoid the leaking and dripping associated with the liquid lubricants. Renewable and bio-based greases are desired but natural oils do not sufficiently structure the thickener leading to phase separation and early oiling out of grease compositions. Esterified propoxylated glycerol base oils utilizing diacids and hydroxy functional acids should have the viscosity and functional affinity for the thickener in a grease formulation limiting or eliminating the phase separation seen with other natural base oils.

Process oils or rubber extender oils are special mineral oils derived from refining base oils, mainly as a mixture of naphthenic, aromatic and paraffinic compounds. Process oils have low volatility, low oxidation, high saturation and color stability. They increase the stability and purity of finished products, making them suitable for application in industries such as tire, rubber, personal care products, polymers and textiles. They also have application as a raw material or as a processing aid for materials. In the tire and rubber industries, process oil and rubber extender oils functions as an internal lubricant to improve the blending of rubber formulations and can be used to make products softer, more flexible and even provide insulating properties. The demand for weather-resistant, flexible rubber products makes process oils and rubber extender oils an important ingredient in the production of automotive tires and other rubber products. Process oils make products softer, more flexible and even provide insulating properties. The demand for weather-resistant, flexible rubber products makes process oils an important ingredient in the production of automotive tires. Process oils also find use in the personal care industry. They lubricate, soften, smooth, extend, moisturize and add emollience to the finished product. Natural oils suitable for low temperature applications tend to consist of significant amounts polyunsaturated fatty acids (PUFA). PUFAs compete during the vulcanization process with multiple components of a functional rubber compound. Esterified propoxylated glycerol oils do not require PUFA to maintain suitable pour points and will not compete with rubber components during the vulcanization process. It has been found that natural oils can provide performance advantages in tire formulations. Specifically, natural oils, such as soybean oil, have been found to lower the glass transition of tires creating better cold weather performance. The use of esterified propoxylated glycerol oils enable tailoring of the performance by lowering the glass transition while optimizing the degree of unsaturation such that an optimal degree of reaction into the formulation can occur. This may include high levels of unsaturation or even completely saturated fatty acids.

Dielectric fluids are used to cool, insulate and protect the internals of electronic devices. Typically, these fluids are used in transformers, capacitors, switches, etc. When used in a transformer, for example, dielectric fluids transport heat from the windings and core of the transformer or connected circuits to cooling surfaces. Where natural oils are susceptible to oxidation and tend to crystallize at ambient outdoor temperatures, esterified propoxylated glycerol base oils are not susceptible to the same degree of oxidation and possess pour points well below those of natural oils.

The lubricant base oil should be miscible with other base fluids for example the mineral oils commercially available as Group I, II, III, and III+ base oils, polyaplhaolefins commercially available as Group IV base oils, and naphthenic, polyalkylene glycol, and esters base oils commercially available as Group V base oils. The lubricating base oil of the present invention may be blended as an additive or compositional modifier to enhance the performance of the formulated base oil. The synthetic lubricant compositions of the present disclosure show high performance and high temperature stability and have lubricating and viscometric properties that exceed those of a mineral lubricating oil. The compositions may comprise other conventional oil additives, e.g. antisludge agents, extreme pressure agents, viscosity modifiers, and antioxidants known in the art.

The composition of the present disclosure is illustrated by the following examples.

EXAMPLES

Examples 1-72

Mapping Compositional Space of Esterified Propoxylated Glycerol(s)

Figure 2:
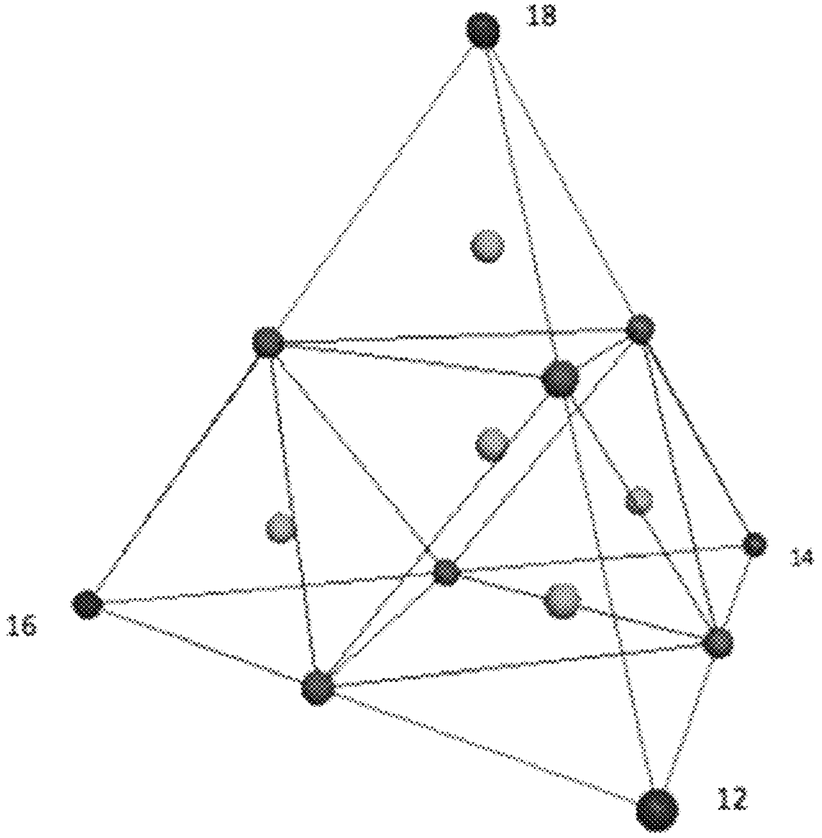
FIG. 2 shows a wireframe rendering of the 3D design space utilized in the demonstration of Examples 1-72.

Given four pure fatty acids (lauric, myristic, palmitic, stearic) we demonstrate the property effects of compositional changes as a function of degree of propoxylation. With 24 example compositions per level of propoxylation (3, 5, 10) we can map property effects across all compositions within the three-dimensional design space for each level of propoxylation as shown in FIG. 2, which shows 3D design space with single fatty acid triesters at the vertices. The results of the mixture design and analysis can be seen in Tables A-C, see FIGS. 3-5. Examples 34, 45, 53, 58, 69 have pour points above 30° C. and were not analyzed for kinematic viscosity.

Figure 6:
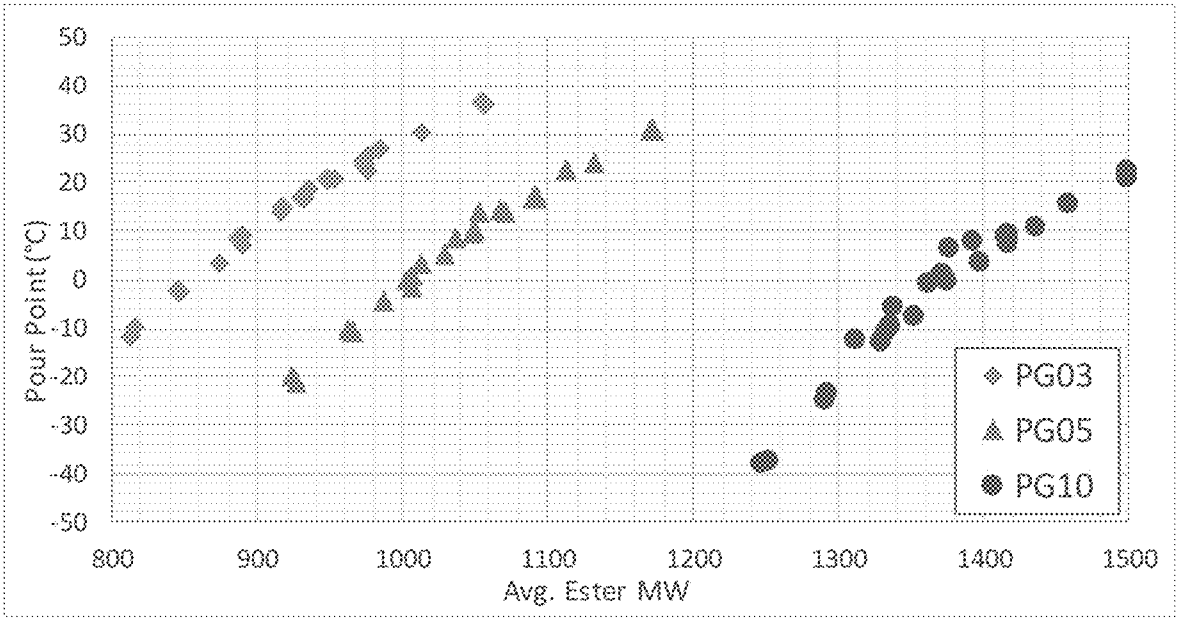
FIG. 6 shows pour point data for examples 1-72 as a function of molecular weight.
Figure 7:
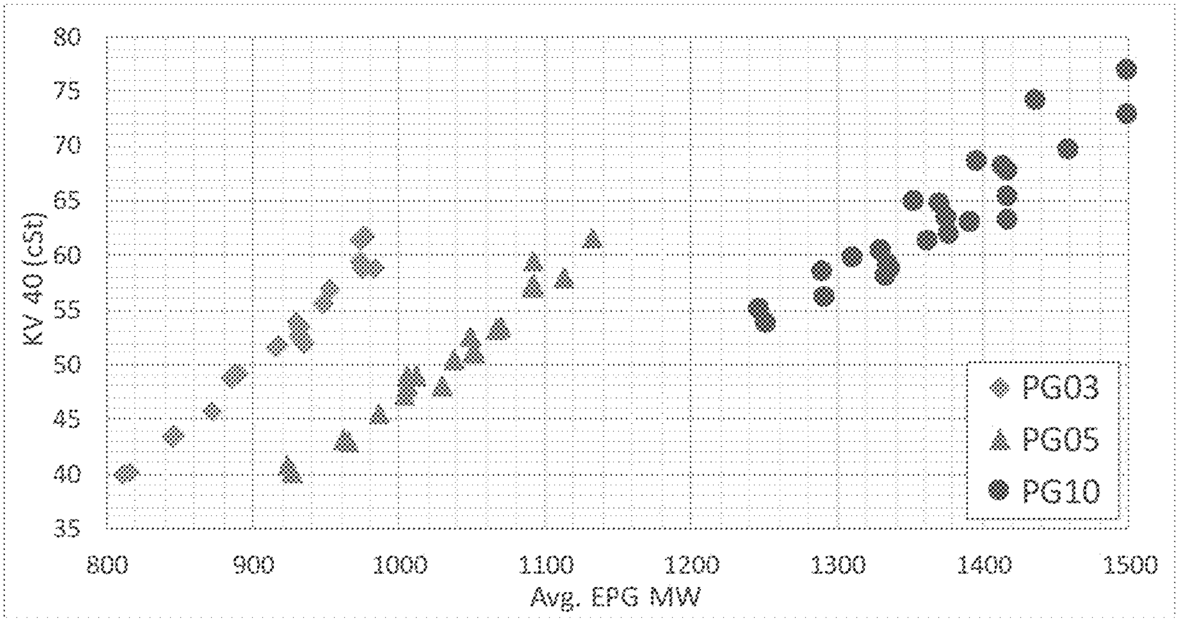
FIG. 7 shows kinematic viscosity (40° C.) data for examples 1-72 as a function of molecular weight.
Figure 8:
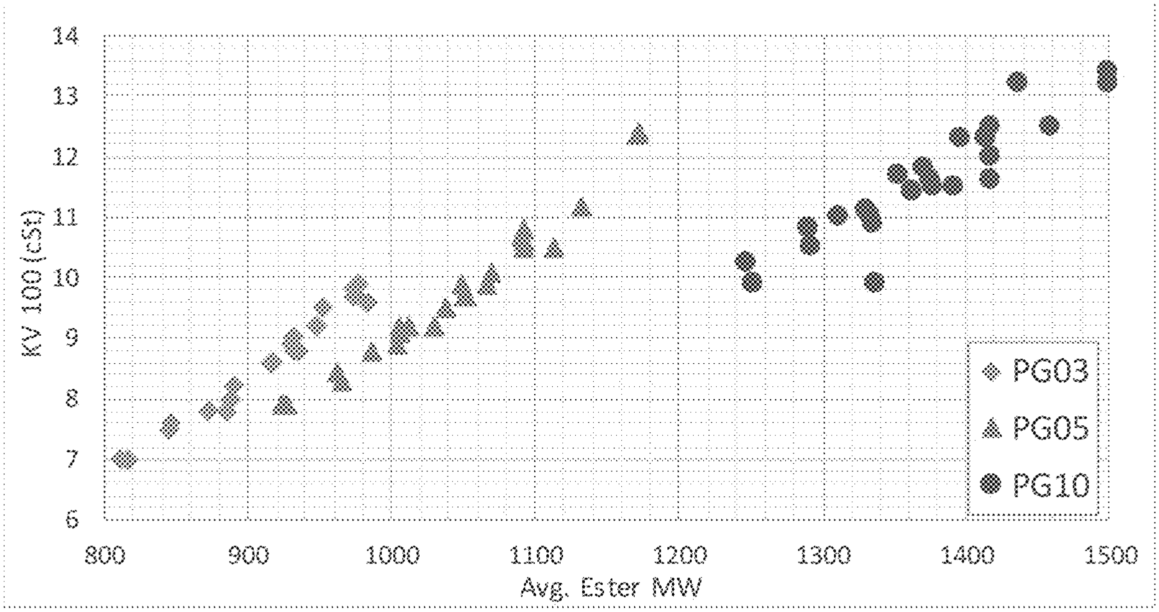
FIG. 8 shows kinematic viscosity (100° C.) data for examples 1-72 as a function of molecular weight.

Average molecular weight was calculated from the fatty acid content and the molecular weight of the propoxylated glycerol. The pour point, see FIG. 6, pour point data vs. average molecular weight for Examples 1-72, and kinematic viscosity data, see FIG. 7 Kinematic viscosity (40° C.) data vs. average molecular weight for Examples 1-72 and FIG. 8 Kinematic viscosity (100° C.) data vs. average molecular weight for Examples 1-72, were plotted against average molecular weight to observe relative effects of changing fatty acid composition and degree of propoxylation. By increasing degree of propoxylation molecular weight increases leading to increased viscosity while simultaneously depressing pour point for comparable fatty acid compositions. FIG. 3 shows Table A, which describes examples 1-24; FIG. 4 shows Table B, which describes Examples 25-48; and FIG. 5 shows Table C, which describes Examples 49-72.

Mapping of the compositional space enables predictive modelling of compositions based on desired performance outputs of the given esterified propoxylated glycerol materials.

Examples 73-79

Base Oil Comparison Versus Commercial Formulated Lubricant

Examples 73-79, see FIG. 9 Table D, consist of esterified propoxylated glycerol base oils prepared as known to those of skill in the art and consisting of fatty acids that are purified sources or whole cut sources. The example base oils (neat and non-additized) were compared against John Deere's HyGard Transmission and Hydraulic Oil which is the standard fluid for meeting the J20c specification for agricultural equipment (Table D).

Esterified propoxylated glycerol lubricating base oils display viscosities characteristic of oils in a given ISO VG range and viscosity indices exceeding commercial mineral oil lubricants. Pour point(s) of the example base oils are also characteristic of fully formulated commercial lubricants.

Examples 80-84

Functional Fatty Acid Modified Esterified Propoxylated Glycerol

Examples 80-84 consist of esterified propoxylated glycerol base oils in which the fatty acid composition has been modified by the addition of diacid components and hydroxy fatty acid components, see FIG. 10 Table E and FIG. 11, Representative functional fatty acids: azelaic, sebacic, and 12-hydroxystearic acids). Example 80 is a base consisting of hydrogenated coconut fatty acids. Examples 81 and 82 consist of hydrogenated coconut fatty acids modified with sebacic (C10) diacid. Examples 83 and 84 consist of hydrogenated coconut fatty acids modified with 12-hydroxystearic acid. Pour point and viscosity of the resultant base oils of the disclosure are clearly impacted by the inclusion of functional fatty acids in the base oil composition.

Example 85

Dielectric Measurements

Example 85, see FIG. 12, consists of esterified propoxylated glycerol base oil, comprising propoxylated glycerol (10 PO) and oleic acid, that was tested for properties characteristic of dielectric fluids, particularly those utilized as transformer fluids. The base oils of the disclosure were compared to commercially available biodegradable transformer fluids, see FIG. 12, Table F.

Examples 86-88

Ethoxylated Glycerol Samples

Examples 86-88 consist of esterified ethoxylated glycerol composed of ethoxylated glycerol Lumulse® 12 (12 ethoxylate units per glycerol) with coconut fatty acids (Example 86), stearic acid (Example 87), and lauric acid (Example 88). Initial pour point analysis and kinematic viscosity analysis is shown in see FIG. 13, Table G.

There has been a growing need and desire for environmentally friendly lubricants whether out of a sense of environmental stewardship or due to mandate based on applications and application areas, but current environmentally friendly options are either too costly or have marked performance issues. Esterified propoxylated glycerol lubricating base oils provides a high-performance environmentally friendly lubricant that is cost comparable to Group III+ mineral oils with performance that exceeds the most costly synthetic lubricants.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to “one embodiment”, “an embodiment,” “an example embodiment,” means that a particular feature, structure or characteristic described in connection with the embodiment is included in at least one embodiment of the present disclosure. Thus, appearances of the phrases “in one embodiment,” “in an embodiment,” or “an example embodiment” in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the disclosure. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

The key differentiation between the present invention and the prior art is the use of alkoxylated glycerol as a polyol for synthetic esters. Fatty acids ≥C8 and alkoxylated glycerols with a degree of alkoxylation ≥3 are used to control the biobased content and biodegradation of the resultant synthetic ester. Additionally, tailoring the fatty acid and alkoxylated glycerol composition is found to allow for tailoring the hydrolytic and the thermo-oxidative stability of the alkoxylated glycerol ester.

The assumption of the instability of the hydrogen at the beta position of the primary esters on glycerol resulted in the failure of previous endeavors to attempt to reduce alkoxylated glycerol ester lubricants to practice, instead focusing on the alkoxylation of neopentyl polyols. In U.S. Pat. No. 3,530,070, the authors describe the synthesis of four propoxylated polyol esters but reduce only one composition to practice, a propoxylated (14 PO) TMP esterified with fatty acids with an average length of C8. In this patent, no measurements of lubricating performance of glycerol-based materials are made or disclosed beyond the measurement of the viscosity and pour point. As a result, the public has not yet had the opportunity to enjoy the benefit of alkoxylated glycerol ester base oils. The current disclosure has observed the unexpectedly high stability of the propoxylated glycerol ester molecules and reduced the lubricants to practice with detailed studies of compositions and formulated lubricants.

The present disclosure describes a method of modification and composition(s) of glycerol esters wherein the glycerol is alkoxylated and esterified to enhance oxidative, thermal, and hydrolytic stability compared to the unmodified glyceride while possessing pour points and viscosity indices required of lubricating oils in general. Further, the authors have found the performance of the formulated propoxylated glycerol ester base oils to exhibit lubricant properties superior to comparable commercial formulated base oils, see FIG. 26, Table 12, especially when compared to environmentally acceptable base oils. Base oils are used to manufacture products including hydraulic fluids, turbine oils, compressor fluids, lubricating greases, motor oils and metal processing fluids. Synthetic ester, including alkoxylated glycerol ester, lubricating oil compositions may comprise other conventional oil additives in the formulated lubricant.

The inventors have discovered that substantially complete alkoxylation of glycerol hydroxyl groups allows for the production of a biodegradable, glycerol derived ester base oil with increased stability of the ester and reduced molar density of the ester bonds within the base oil. In a triglyceride, the two primary esters have a methine proton in the beta position relative to the ester bonds, see FIG. 14 at A. By reacting alkoxy linkages (ethers) onto the glycerol before the fatty acid esterification, FIG. 14 at B, now the protons in the beta position relative to the ester are more stable methylene protons. It is expected that when the degree of alkoxylation is ≥3 (on glycerol), the alkoxy groups will have reacted with the primary hydroxyl groups of the glycerol and the resultant alkoxylated glycerol esters will possess enhanced stability compared to esters of glycerol due to substantial coverage of the primary hydroxyl groups of the glycerol. Further it is expected that esters with a degree of alkoxylation ≥5 will have an enhanced stability relative to esters with a degree of alkoxylation ≥3. The enhanced stability of an ester when the degree of alkoxylation is ≥5 is due to the complete coverage of the glycerol hydroxyl groups. When all glycerol hydroxyls are alkoxylated, the subsequent ester bonds will have only β methylene protons, whereas partial reaction of the glycerol hydroxyls allows for the occurrence of β methine protons. Further, all β methylene protons will be stabilized by the adjacent ether groups. Ether bonds can only be hydrolyzed by strong haloacids. Ether molecules are unable to form hydrogen bonds with each other and are stable compounds, whereas esters can form hydrogen bonds making them relatively less stable. Additionally, ether bonds are electron donating. As such, the glycerol methine proton of the alkoxylated glycerol ester is more strongly bound to the glycerol. Further, the ether bond will stabilize the beta-methylene proton on the alkoxylated glycerol ester.

In addition to stabilizing the methine proton (on the secondary carbon) of the glycerol, the polyether spacers also physically separate and isolate the ester bonds away from the glycerol. This limits the formation of the transition state six-membered ring with the methine group of the glycerol that is understood to enable the thermal degradation of triglyceride oils (glycerol esters). [Rudnick, L. R. (ed.). (2020). *Synthetics, Mineral Oils, and Bio-Based Lubricants* (pp. 60). CRC Press] The instability of the beta-hydrogen in glycerol esters due to the adjacent ester groups has been resolved by inserting the stabilizing polyether spacers. The new beta-positioned hydrogen atoms are located on the ester-adjacent alkoxy groups surrounded by stabilizing ether groups.

When the terminal alkoxy group of an alkoxylated glycerol ester is a propoxy or butoxy group, the alkoxylated glycerol ester is significantly more stable than the glycerol ester because the hydroxyl groups of propoxy and butoxy groups are all secondary alcohols compared to the 2 primary and 1 secondary hydroxyl groups on the glycerol. It is well known that secondary hydroxyl groups produce a more stable ester bond compared to an ester of a primary hydroxyl group. This can be attributed to the strain induced on the carbon backbone which helps to inhibit the formation of the transition state six-membered ring that enables the thermal decomposition of esters. Esterification of an alkoxylated glycerol which is terminated with a propoxy or butoxy group creates a more sterically hindered and electronically stable secondary ester bonds compared to glycerol esters. It should be noted that an ethoxylated glycerol ester will have primary esters but may still exhibit greater stability than the analogue glycerol ester.

Further stabilizing the alkoxylated glycerol ester oil of this disclosure, the beta-hydrogens of the alkoxylated glycerol ester are methylene hydrogens. It is known to those skilled in the art that hydrogen bond stability decreases in order of methyl>methylene>methine. The classic "beta-hydrogen argument" against glycerol backbone chemistry in a base oil is the result of a primary ester abstracting a methine hydrogen of the beta-carbon. In one embodiment, the propoxylated glycerol ester has a degradation mechanism that is based on a secondary ester abstracting a methylene hydrogen of the beta-carbon, now located at the terminal propoxy unit. The resulting propoxylated glycerol ester oil(s) of this disclosure comprises a stabilizing polyether spacer (polyalkoxy) between the glycerol and fatty acid(s) of a triglyceride oil.

Further, a method for controlling the thermal, oxidative, and hydrolytic stability of an alkoxylated glycerol ester is found in increasing the molecular weight of the alkoxy groups thereby reducing the overall molar density of ester bonds in the alkoxylated glycerol ester compared to the glycerol ester. As the ester bond tends to be the weak link in the degradation of a synthetic ester, the thermal, oxidative, and hydrolytic stability are improved when the number of ester bonds is decreased.

Oxidative stability for commercial and industrial materials is often conducted according to the Rotating Pressure Vessel Oxidation Test (RPVOT) as specified in ASTM D2272. The RPVOT results can be used to compare relative stability of base oils in the presence of water, oxygen, catalyst, and heat. RPVOT was performed to evaluate the thermo-oxidative stability of glycerol ester and propoxylated glycerol ester base oils. In this test, longer lifetimes equate to more stable base oils and oil formulations. FIG. 17, Table 3 compares the RPVOT data of two natural glycerol esters, one trimethylolpropane (TMP) ester, and two propoxylated glycerol esters without any additives to enhance performance. This data confirms that an increase of greater than 60% can be observed in the overall stability of the propoxylated glycerol esters (both saturated and unsaturated) when compared to glycerol esters. The TMP ester, despite its lack of a beta-proton, performs relatively poorly in this test. In formulated lubricant systems, propoxylated glycerol esters were found to have RPVOT lifetimes in the same order of commercial petroleum-based turbine oils, see FIG. 26, Table 12. When compared to formulated natural glycerol ester lubricants, the propoxylated glycerol ester turbine lubricant was shown to have between a 375% and a 1000% increase in lifetime. Further, it is shown in Table 12 that the propoxylated glycerol ester turbine lubricant has a superior Oxidative Onset Temperature (OOT), as measured by ASTM E2009-08, compared to the Chevron GST. TMP trioleates are shown in literature to have OOT of 156° C. and after formulation, up to 206° C. [Wu, Y., et al; *Thermochimica Acta,* 569, 2013, pp. 112-118]. While this high level of thermal and oxidative performance for the alkoxylated glycerol is surprising, it should be noted that it is possible for a biodegradable base oil to be too stable, specifically with respect to hydrolytic stability.

The control of the molar density of the ester bonds through the degree of alkoxylation of the alkoxylated glycerol ester allows for the tailoring of the hydrolytic stability, which is a critical tool in the development of optimized biodegradable base oils. It is well understood that the first step in biodegradation in a natural or synthetic ester is the hydrolysis of the ester bond. As such, an oil with extremely high hydrolytic stability could be expected to fail the OECD 301B biodegradability test. A well-designed environmentally acceptable oil would optimize hydrolytic performance by tailoring the stability of ester bond and controlling the molar ester density to achieve the maximum hydrolytic stability of the base oil while still passing the OECD 301B biodegradability test. For current OECD 301B requirements, a "Readily Biodegradable" material must exhibit at least 60% degradation within the 10-day window which starts once 10% degradation is observed. The most optimized hydrolytically stable biodegradable base oils would show a degradation at or just greater than 60% on day 10 of the window. FIG. 23, Table 9 shows an example with an optimized ester density. It is expected that the base oil of the present invention will meet or exceed the thresholds of other common biodegradation tests While passing the OECD 301B, FIG. 18, Table 4 shows the excellent performance of the propoxylated glycerol esters with regard to their hydrolytic stability. It is worth noting that the performance of the alkoxylated glycerol esters outperforms that of unsaturated polyol esters in hydrolytic stability. The unsaturated polyol esters are known to have similar hydrolytic performance to unsaturated glycerol esters [*Fuels and Lubricants Handbook,* $2^{nd}$ ed., p. 560]. While it is not fully understood why the propoxylated glycerol esters have such a significant improvement in hydrolytic stability, it is clear from the performance that there is a novel effect. Looking at the weight change of the Cu Panel, it can be seen that the saturated propoxylated glycerol esters (Ex. 91 and 103) are 7 to 10 times lower than the saturated glycerol ester (Ex. 92) and the saturated TMP ester (Ex. 90). Further, the Total AV number of the Ex. 103 and 91 were 4 to 7 times lower than the glycerol ester and the TMP ester. An explanation may be found in the alkoxy group itself. US Patent application 20170240833 teaches that polyalkylene glycols are known to improve hydrolytic stability when blended with other base oils and references US Patent Application 20140107004A1 which teaches that blending a triblock polyalkylene glycol at about 10% with vegetable oil or synthetic esters can greatly improve the hydrolytic stability. It is proposed that the increase in hydrolytic stability may be related to latent water, that is water bound by hydrogen bonds to the ether bonds, which is not free to participate in hydrolysis until saturation of the oil is achieved. If this proposed mechanism is correct, it would be just one additional contributing factor to the overall thermo-oxidative and hydrolytic stability.

Melt Thermodynamics

It is known in the art that alkoxylation has the potential to decrease the pour point of an ester. However, the current disclosure has observed a surprising decrease in the melting enthalpy and a marked reduction in the degree of undercooling. The degree of undercooling for a base oil indicates the increase in temperature required to fully melt an oil after crystallization has started. The degree of undercooling for the purpose of this disclosure is described as the difference between the temperature at which a material is fully melted on heating and the temperature at which the material begins to crystallize on cooling [$T_{melt}-T_{onset}$=Undercool] as determined by differential scanning calorimetry (DSC) with a heating and cooling rate of 5° C./min. "Undercooling" and "degree of undercooling" can be used synonymously.

Alteration of the inherent thermodynamics of the esters through alkoxylation enables the production of base oils which are more resistant to crystallization and gelation, and the deleterious effects noted when an oil is handled around and below its pour point. The higher the enthalpy of melting, the more stable the solid form of a given material. Reduced melting enthalpy for a material indicates a less stable crystal structure or an increase in the amount of an amorphous phase. In either case, the result is that less heat is required to re-melt a solidified material. Further, it has been shown that in some alkoxylated glycerol esters the reduction in the melt enthalpy has been reduced to the point that no crystallization is observed by DSC and no cloud point is distinguished during testing.

The thermodynamic properties of a given base oil can be thoroughly examined using DSC in addition to traditional qualification testing (e.g. cloud point and pour point). For materials examined in this patent, the pour point (modified ASTM D97), cloud point (modified ASTM D2500), and onset of crystallization (DSC) were observed. When operating conditions drop below the pour point of a given lubricant, the oil will gel or freeze. If two oils have similar pour points, an oil with a lower melt enthalpy and a reduced degree of undercooling will recover to a fluid state at a lower temperature and in less time compared to the oil with a higher enthalpy and greater undercooling. Esters of alkoxylated glycerols, when compared to natural esters and neopentyl polyol esters, were found to exhibit reduced enthalpy and undercooling which resulted in faster melting behavior. Representative comparisons of natural esters, neopentyl polyol esters, and alkoxylated esters are described in the examples of the present disclosure.

The ASTM required equipment for ASTM D97 and ASTM D2500 were modified as follows: Cold baths were prepared in cylindrical stainless-steel thermoses (dimensions 70 mm×110 mm) and filled with isopropyl alcohol. Bath temperatures, as described by the ASTM, were reached and maintained through manual addition of dry ice. To serve as the cooling jacket, a test tube (25×150 mm; OD×length) with a 25×25 mm piece of fabric cushion placed at the bottom was set to cool in the IPA/$CO_2$(s) baths. 8 ml of the specimen was charged in a sample tube (15×150 mm; OD×length). A low temperature thermometer (down to −100° C.) through a rubber stopper (one-hole stopper with a tight fit on thermometer) was placed into the sample tube such that the thermometer bulb sits below the meniscus of the sample liquid without touching the test tube. The sample tube is then placed into the cooling jacket and held upright and kept near vertical in position. The test samples were monitored and pour points/cloud points were recorded per the ASTM directions.

A single melt event is also noted for esters of alkoxylated glycerols utilizing DSC. Natural esters and esters of neopentyl polyols tend to show exothermic events near their melt transitions indicating the formation of a more stable and higher melting crystalline solid.

Oils which exhibit multiple melt phase transitions can also suffer from the growth of high stability crystal phases when the oil is thermally cycled close to the onset of crystallization. This well-known phenomenon occurs due to the increased thermal stability of the high melting crystal phase particles, which remain after partial melting (the particles serve as seed crystals).

Oils with a lower undercooling require a smaller increase in temperature after crystallization to melt the oil and erase the oil "memory." Shelby and Miller teach the concept of oil "memory" as a result of gels or crystals not fully dissociating even when above the melt point, so that on a second cooling cycle, gelation or crystal growth occurs much more quickly and at higher temperatures. If two oils have the same crystallization onset temperature, the oil with the lower undercooling will fully melt at a lower temperature and erase the oil "memory". While propoxylated glycerol esters have undercooling values on the order of 10° C., triglycerides exhibit a degree of undercooling on the order of 20-40° C. The effect of this is that glycerol esters and polyol esters must be heated substantially above the onset of crystallization in order to melt the oil before use. See, Selby, T. and Miller, G., "Thermal History of the Engine Oil and Its Effects on Low-Temperature Pumpability and Gelation Formation," *SAE Technical Paper* 2008-01-2481, 2008, https://doi.org/10.4271/2008-01-2481 FIG. 19, Table 5 shows this effect with 4 examples that are all based on trilaurate esters. At 5° C. above the onset of crystallization temperature, 100% of Ex. 92 (glycerol ester) is solid; 31% of Ex 93 (PG3 ester) is solid; 18% of Ex. 94 (PG10 ester) is solid; and 81% of Ex 90 (TMP ester) is solid. At 10° C. above the crystallization onset temperature, DSC measurements show almost no solids (less than 4%) for the propoxylated glycerol esters, while the glycerol ester has not melted at all and the TMP ester is 46% solid. From this data, it is clear that propoxylated glycerol esters have an unexpectedly low temperature recovery from excursions below the pour point or cloud point.

Blown Oil

Blown oils are drying oils which have been modified through an oxidative process at elevated temperatures and are manufactured to a specific viscosity specification ranging from 1 poise @25° C. up to 1600 poise @25° C., depending on the oil type. The oxidation process leads to chemically modified products containing polymerized triglyceride esters incorporating additional combined oxygen. Peroxide, hydroperoxide and hydroxyl groups are also present. The oxidation process also modifies properties such as specific gravity, solubility, and reactivity.

The blown, stripped oil blend can be used for end-use applications that require or take advantage of oils having high flash point and increased viscosity. For example, the blown, stripped oil blends are particularly suitable for dedusting fluids. Blown oils also find uses in many lubricant applications including cutting fluids, rolling and metal working oils, drilling muds, two stroke engine oils, greases, wire drawing, and chainsaw lubricants. Blown oils degrade slower than petroleum based mineral oils having lower flash points.

The current disclosure, in one aspect, provides a synthetic lubricating base oil. The base oil may include an ester of an alkoxylated glycerol with an average degree of alkoxylation ≥3, such as greater than or equal to 4, 5, 6, 7, 8, 9, 10, etc. and at least one fatty acid having ≥8 carbon atoms, such as greater than or equal to 9, 10, 11, 12, 13, 14, 15, 16, 17, 18, etc., wherein the melting enthalpy has been significantly decreased and the undercooling has been decreased. In many cases, the melt enthalpy for propoxylated glycerol esters with an average degree of alkoxylation ≥3 has been reduced by >50% relative to the triglyceride with the similar fatty acid composition, see Table 5. When the degree of propoxylation is approximately 10, the melt enthalpy is reduced by 70-80% relative to the analogous triglyceride, see Table 6. Samples with lower enthalpies, below 15 J/g, were visually observed to have reduced crystallization and greater transparency upon solidifying compared to samples with enthalpies over 15 J/g. It has been observed for propoxylated glycerol esters which have fatty acid compositions with higher levels of low melt point fatty acids, such as oleic, linoleic, capric, and caprylic acid, and levels of propoxylation greater than 3, more preferably greater than 5, and even more preferably 10 or greater, that the enthalpy of the lubricant is reduced to the point that there is no visual observation of crystallization. In these samples, no cloud point was recorded, and transparency remained well below −50° C. By decreasing the level of propoxylation, ex. from 10 to 5, or decreasing the relative concentration of the low melt point fatty acids which comprise the propoxylated glycerol ester, transparent samples were observed to transition to translucent samples. This can be observed in FIG. 21, Table 7. In addition to full propoxylated examples, it was observed that some alkoxylated samples, which were propoxylated and capped with an ethoxy group before esterification were also translucent. It should be noted that when the enthalpy of melting drops below about 15 J/g, the integration points in DSC thermograms become difficult to define and observable crystallization peaks can be difficult to measure or even visually observe.

In many cases, the undercooling for propoxylated glycerol esters with an average degree of alkoxylation ≥3 has been reduced by more than 15° C. relative to the triglyceride with similar fatty acid composition, see FIG. 20, Table 6. When the degree of propoxylation is approximately 10, the degree of undercooling may be reduced by more than 20° C. relative to the triglyceride with a similar fatty acid composition. Fatty acid compositions of propoxylated glycerol esters which already exhibit a low degree of undercooling as a triglyceride, such as coconut oil, show a lower decrease in undercooling. A decrease in undercooling due to the addition of a propylene glycol spacer between the glycerol and the fatty acid can be observed with a greater than 30% decrease in the undercooling of the bulk phase, more preferably with a greater than 50% decrease, more preferably with a greater than 70% decrease, and even more preferably with a greater than 75% decrease. Indeed, specific decreases of 76.1%, 38.3%, 77.7%, 67.2%, 81.3%, 74.8%, 72.7% are considered within the scope of this disclosure.

In general, the bulk crystallization of the material is the intent of the above teaching and the temperature of the onset of crystallization of the bulk phase is used in determining the degree of undercooling. It is understood that the addition of another component with higher melt point can change the measured undercooling. This minor phase is not used as the onset of crystallization; however, a note is made to differentiate this minor crystallization from the bulk phase crystallization.

In addition, the alkoxylate may be ethylene oxide, propylene oxide, butylene oxide, or a combination thereof.

It is well known that the polarity of the alkoxylated glycerol is highly dependent on the ratio of EO, PO, and BO utilized in the polyether segments. Alkoxylated glycerols that are high in EO will have increased polarity leading to a high level of solubility in water, whereas increasing the amount of PO produces a less polar alkoxylated glycerol ester with greater oil solubility. It is also known that exceeding a certain number of EO groups in a block can create issues with the crystallization of the EO blocks. This ratio of EO-PO allows for significant control in the development of surfactants. Polyalkylene glycol (PAG) lubricants have taken advantage of this characteristic and were originally used in water-based lubricants. More recently, commercially available PO/BO and BO lubricants have been introduced. In U.S. Pat. No. 10,160,928 B2, it is disclosed that BO decreases issues associated with the demulsification of the UCON OSP lubricants.

Alkoxy groups with increased EO/PO ratios have greater water solubility. Additionally, it has been seen that the demulsification of the propoxylated glycerol ester can be difficult, depending on the degree of propoxylation and the fatty acid composition. As such, it would be expected and claimed that a lubricant which is a PO/BO glycerol ester or even a BO glycerol ester would be expected to have improved performances with specific regard to oil solubility and demulsification.

In addition, it is understood by those skilled in the art that there are a range of additives which have varying degrees of effectiveness toward improved demulsification and that these dependencies include the base oil and the overall oil formulation. Included in these additives would be those that are already known to be effective as demulsifiers in base oils that are triglyceride based, synthetic ester based, polyalklene glycol based, or other Group I, II, III, or IV base oil based. U.S. Pat. No. 6,495,188 teaches the presence of ethoxy groups to adjust the emulsion stability of a propoxylated glycerol ester and likewise, the replacement of some propoxy groups with other alkoxy groups having greater hydrophobicity would increase overall hydrophobicity.

The inventors have produced ethoxylated glycerol esters with similar molecular weights to the propoxylated glycerol esters, within about 6%. The ethoxylated glycerol exhibited very similar viscosities with higher viscosity indices compared to the propoxylated glycerol esters with the same fatty acid composition, see FIG. 27, Table 13. Further, the pour point of the ethoxylated glycerol esters were elevated by over 20° C. This can be explained by the greater polarity of the ethoxy groups compared to the propoxy groups. The solubility of water was found to be significantly higher in the ethoxylated glycerol esters than the propoxylated glycerol esters. It was observed EO samples had 6.04% water solubility while the PO samples had a solubility of 0.58%, as determine by Karl Fischer titration at room temperature. As such, it would be expected that a base oil which is an alkoxylated glycerol ester, wherein the alkoxylate is a blend of PO/BO or even BO only, would be expected to have improved performance with specific regard to oil solubility and demulsification. As such, it is understood by those skilled in the art that in one embodiment optimal base oil design may prefer the use of an ethoxylation of the glycerol; whereas, in another embodiment for a base oil, it may be preferable to use a butoxylation of the glycerol.

The alkoxylated polyol may be propoxylated glycerol preferably with a range from 3 to 20 propoxy groups per molecule, more preferable is a range of 5 to 12, more preferable is a range of 8 to 11, more preferable is a degree of propoxylation of 10.

Various sources for the fatty acid are possible. In one instance, the fatty acid is substantially whole cut. Further yet, at least one fatty acid source may substantially be whole cut. Whole cut fatty acids are products of the direct fat splitting of natural oils and substantially comprise the native fatty acid composition of a representative natural oil. For the purposes of this disclosure, the whole cut fatty acid may be "cleaned" as understood by those skilled in the art and/or partially fractionated. Further, specific cuts, such as for purpose of example only but not intended to be limiting, high melt point cuts, may also be employed. Suitable whole cut fatty acids may be derived from vegetable or seed oils such as coconut oil, palm oil, palm kernel oil, palm fatty acid distillate, soybean oil, jatropha oil, rapeseed oil, canola oil, high oleic soybean oil, sunflower oil, high oleic sunflower oil, corn oil, cottonseed oil, castor oil, olive oil, safflower oil, or linseed oil. Further, the source for the fatty acid is fractionated or topped coconut oil, palm kernel oil, tallow, or palm oil. Whole cut fatty acids may also be derived from animal oils such as fish oil, lard, tallow, or whale oil. Even further, the oil may include multifunctional fatty acids which may consist of dicarboxylic acids, hydroxy functional acids, or acids modified by techniques that may include but are not limited to epoxidation, maleination, metathesis, amidation, halogenation, hydration, hydroformylation, dimerization, or estolide formation. Even further, pure fatty acid stream may be used, such as caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, oleic acid, linoleic acid, and erucic acid. Further, functional acids such as undecylenic acid are understood to be included in this work.

Fatty acids obtained by high-pressure splitting of plant oils are distilled and can be fractionated into various fractions or individual cuts. Fractionation makes it possible to separate the fatty acid mixtures into narrower cuts or even individual components. Topped describes the removal of a lower boiling fraction from the fatty acid mixture. Further, the fatty acids may be from hydrogenated oils. Further, the fatty acid may be a dicarboxylic acid such as oxalic acid, malonic acid, succinic acid, glutaric acid, adipic acid, pimelic acid, suberic acid, azelaic acid, sebacic acid, undecanedioic acid, dodecanedioic acid, or octadecanedioic acid.

More than one fatty acid may be employed, and the fatty acid may be a functionalized acid. Functionalization of a fatty acid may occur before or after esterification to the alkoxylated glycerol. Functionalization may comprise epoxidation, maleination, metathesis, amidation, halogenation, hydration, estolide formation, hydroformylation, dimerization, or vulcanization. Specifically, the functionalized acid may be saturated or unsaturated, such as a saturated functionalized acid such as 12-hydroxystearic acid. The structure of the fatty acid may vary as well. The fatty acid may be branched, cyclic or aromatic. Branched fatty acids may include but are not limited to 2-ethylhexanoic acid or isostearic acid. The oil will have improved physical properties including a pour point at or below 0° C., preferably below −10° C., preferably below −20° C., preferably below −30° C. and most preferably below −40° C. being disclosed as well.

By utilizing fatty acid(s) in conjunction with alkoxylated glycerol(s), this disclosure generates base oils that have high biobased carbon content (>40%, such as >45, >50, >55, >60, >65, >70, >75, >80, >85, >90, >95, etc.) determined by ASTM method D6866-20, see FIG. 24 Table 10, and high biodegradability (>50%, such as >55, >60, >65, >70, >75, >80, >85, >90, >95, etc.) determined by OECD 301B, see FIG. 23, Table 9. Biobased carbon content refers to materials which are derived from biological products or renewable domestic agricultural materials (including plant, animal, and marine materials) or forestry materials or an intermediate feedstock or agricultural byproduct, such as soapstock. In producing a biobased oil, it is preferable that the polyol used to produce an ester-based lubricant is bio-derived. Bio-derived glycerol would be preferred for this reason. The lubricating base oil may be at least 40 percent biobased carbon, such as for purposes of examples only and not intended to be limiting 45 percent, 50, 55, 60, 65, 70, 75, 80, 85, 90, 95, etc., more preferably the lubricating base oil is at least 50 percent biobased carbon, and most preferably the lubricating base oil is at least 55 percent biobased carbon. Biodegradability refers to the ability of a material to be decomposed by bacteria or other living organisms. The lubricating base oil may be at least 50 percent biodegradable, such as for purposes of example only and not intended to be limiting 55 percent, 60, 65, 70, 75, 80, 85, 90, 95, etc., more preferably the lubricating base oil is at least 50 percent biodegradable, and most preferably the lubricating base oil is at least 60 percent biodegradable. The lubricating base oil may have a molecular weight ≥500 g/mole, preferably ≥600 g/mole, preferably ≥700 g/mole, preferably ≥800 g/mole, and most preferably ≥1000 g/mole and a viscosity index of ≥160, such as 165, 170, 175, 180, 185, 190, 195, 200, or higher. Performance of the oil may also be enhanced by incorporating additives such as antioxidants, anti-wear, anti-corrosion, anti-sludge, anti-foam, demulsifiers, viscosity index improvers, detergents/dispersants, pour-point depressants, alkalinity improvers, friction modifiers, seal swell agents, metal deactivators/complexing agents, and extreme pressure agents. It is understood by those skilled in the art that there are a range of additives which have varying degrees of effectiveness toward improved performance and that these dependencies include the base oil and the overall oil formulation. Included in these additives would be those that are known to be effective as additives in base oils that are triglyceride based, synthetic polyol ester based, polyalklene glycol based, or other Group I, II, III, IV, or Group V based.

The current disclosure provides methods of preparation. For instance, a method of stabilizing the β-hydrogen of glycerol in a base oil wherein the free hydroxyl groups of the glycerol are alkoxylated with ethylene oxide, propylene oxide, butylene oxide, or a combination thereof to form an alkoxylated glycerol. The disclosure also provides a synthetic ester lubricating base oil with improved oxidative, thermal and hydrolytic stability including an ester of alkoxylated glycerol with an average degree of alkoxylation ≥3, and at least one fatty acid having ≥8 carbon atoms. The disclosure also provides a synthetic ester lubricating base oil with improved oxidative, thermal and hydrolytic stability comprising an ester of alkoxylated glycerol with an average degree of alkoxylation ≥3, and at least one fatty acid having ≥8 carbon atoms. Further, the alkoxylated glycerol may be propoxylated preferably with a degree of propoxylation of 10. Also, a source for at least one fatty acid may be substantially whole cut. The source for the fatty acid may be coconut oil, high oleic soybean oil, soybean oil, corn oil, canola oil, sunflower oil, or rapeseed. The source for the fatty acid may be fractionated or topped coconut oil, palm kernel oil, tallow, or palm oil. The at least one fatty acid may be a dicarboxylic acid. The dicarboxylic acid may comprise adipic acid, azelaic acid, or sebacic acid. The at least one fatty acid may be a functionalized acid. The saturated functionalized acid may include 12-hydroxystearic acid, 2-ethylhexanoic acid, or isostearic acid. The functionalization may comprise epoxidation, maleination, metathesis, amidation, halogenation, hydration, estolide formation, hydroformylation, dimerization, or vulcanization. At least one fatty acid may be branched. The branched acid may comprise 2-ethylhexanoic acid, or isostearic acid. The lubricating base oil may have a pour point at or below −10° C. The lubricating base oil may be at least 60 percent biodegradable. The lubricating base oil may be at least 50 percent biobased. The molecular weight may be ≥1000 g/mole. The lubricating base oil may have a viscosity index of ≥160. Further, the disclosure provides a synthetic lubricant that includes a significant proportion of the synthetic ester lubricating base oil and may contain an additive selected from antioxidants, anti-wear agents, anticorrosion agents, anti-sludge agents, and/or extreme pressure agents. Further, the disclosure provides a lubricating base oil or blown oil that may be modified through an oxidative process at elevated temperatures.

The current disclosure may also provide a method of stabilizing the β-hydrogen of glycerol in a base oil where the free hydroxyl groups of the glycerol are alkoxylated with ethylene oxide, propylene oxide, butylene oxide, or a combination thereof to form an alkoxylated glycerol. The base oil may have improved oxidative, thermal and hydrolytic stability comprising an ester of alkoxylated glycerol with an average degree of alkoxylation ≥3, and at least one fatty acid having ≥8 carbon atoms. The alkoxylated glycerol may be propoxylated preferably with a degree of propoxylation of 10. A source for at least one fatty acid may be substantially whole cut. The source for the fatty acid may be coconut oil, high oleic soybean oil, soybean oil, corn oil, canola oil, sunflower oil, or rapeseed oil. The source for the fatty acid may be fractionated or topped coconut oil, palm kernel oil, tallow, or palm oil. The at least one fatty acid may be a dicarboxylic acid. The dicarboxylic acid may comprise adipic acid, azelaic acid, or sebacic acid. At least one fatty acid may be a functionalized acid. Functionalization and or hydrogenation may occur before or after reacting the fatty acid to the ester.

The saturated functionalized acid may comprise 12-hydroxystearic acid, 2-ethylhexanoic acid, or isostearic acid. The functionalization may comprise epoxidation, maleination, metathesis, amidation, halogenation, hydration, estolide formation, hydroformylation, dimerization, or vulcanization. At least one fatty acid may be branched. The branched acid may comprise 2-ethylhexanoic acid or isostearic acid. The lubricating base oil may have a pour point at or below −10° C. The lubricating base oil may be at least 60 percent biodegradable. The lubricating base oil may be at least 50 percent biobased. The molecular weight may be ≥1000 g/mole. The lubricating base oil may have a viscosity index of ≥160. The current disclosure also provides a synthetic lubricant that may include a synthetic ester lubricating base oil incorporating an additive selected from antioxidant, anti-wear, anticorrosion, anti-sludge, and/or extreme pressure agents. The current disclosure also provides a blown oil including the synthetic ester lubricating base oil where the lubricating base oil may have been modified through an oxidative process at elevated temperatures. The lubricating base oil may also be part of a cosmetic formulation.

One aspect of the present disclosure is the use of the propoxylated glycerol ester as a lubricating base oil, either neat or as a formulated product, in Industrial Lubricants: gear oils, R&O compressor oils, R&O turbine oils; Automotive Oils: crankcase oils, transmission oils, gear oils; Metal Working Fluids; Marine Lubricants; Grease; Process Oil; or Dielectric Fluids.

The current disclosure may also provide a blown oil blend comprising partial or complete replacement of the synthetic ester lubricating base oil, wherein the lubricating base oil has been modified through an oxidative process at elevated temperatures to produce heat stable, high viscosity base oils. A typical blowing process involves heating the oil to 70 to 120° C. and passing air through the liquid. The modification causes the formation of C—O—C and C—C cross links, and hydroxyl and carboxyl functional groups. The blown oils can be used as additives, as thickeners, or to give surface-active properties to the formulation. They can offer features such as lubricity, biodegradability, high flash point, thickening, and low toxicity.

Lubricant compositions of the present invention have utility in applications where the oil in use has contact with the environment, particularly contact with water, air, and particulate contaminants. Such applications encompass hydraulic fluids for mobile equipment, universal tractor fluids, gear and transmission oils for mining and forestry equipment. With enhanced hydrolytic and thermo-oxidative stability, lubricant compositions of the present invention are suited to applications prone to contamination. Additionally, with biobased and biodegradable compositions, the lubricant compositions of the present invention are suited to applications with high incidence of leaks and oil loss.

Lubricant compositions of the present invention have particular utility as turbine oils for hydropower turbines. Presently, hydropower turbines must utilize mineral based oils as they provide the stability and lifetime desired for the application because common biobased and biodegradable oils fail to meet the stability criteria. The oils of the present invention provide high biobased content, are readily biodegradable, and have thermo-oxidative stability on par with common mineral turbine oils, such as Chevron GST and Shell Turbo T. As such, reduction to practice and formulation development for the oils of the present invention has provided initial data demonstrating the utility of the compositions as hydropower turbine oils. Further embodiments are illustrated in the following Examples, which are given for illustrative purposes only and are not intended to limit the scope of the disclosure.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth to provide those of ordinary skill in the art with a complete disclosure and description of how to perform the methods disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Method A: Charging an appropriate reaction vessel with the alkoxylated glycerol and a 10% molar excess of the required fatty acid(s). The esterification was carried out at 240-250° C. and run under vacuum until the acid value of the reaction mixture was below about 15 mg KOH/g and the hydroxyl value of the reaction mixture was below about 20 mg KOH/g. Excess fatty acid and volatile reaction by-products were then removed via short path distillation under vacuum and elevated temperature. Common ester purification techniques may be utilized in the absence of short path distillation. The ester product of the reaction was purified to an acid value <1 mg KOH/g with a preferred acid value <0.5 mg KOH/g, and a hydroxyl value <10 mg KOH/g with a preferred hydroxyl value <5 mg KOH/g. The alkoxylated glycerol ester is considered a triester when a hydroxyl value of less than 15 mg KOH/g is achieved, or more preferably less than 10 mg KOH/g, or most preferably less than 5 mg KOH/g.

Method B: The alkoxylated glycerol ester lubricant base oils of the present disclosure were prepared by charging an appropriate reaction vessel with the alkoxylated glycerol, a 10% molar excess of the required fatty acid(s), and 0.5 mole % methanesulfonic acid. The esterification was carried out at 170° C. and run under vacuum until the acid value of the reaction mixture was below about 15 mg KOH/g and the hydroxyl value of the reaction mixture was below about 10 mg KOH/g. Excess fatty acid and volatile reaction by-products were then removed via short path distillation under vacuum and elevated temperature. Common ester purification techniques may be utilized in the absence of short path distillation. The ester product of the reaction was purified to an acid value <1 mg KOH/g with a preferred acid value <0.5 mg KOH/g, and a hydroxyl value <10 mg KOH/g with a preferred hydroxyl value <5 mg KOH/g.

Method C: The alkoxylated glycerol ester lubricant base oils of the present disclosure were prepared by charging an appropriate reaction vessel with the alkoxylated glycerol, a 0.1% molar deficiency of the required fatty acid(s), and 0.5 mole % methanesulfonic acid. The esterification was carried out at 170° C. and run under vacuum until the acid value of the reaction mixture was below about 3 mg KOH/g and the hydroxyl value of the reaction mixture was below about 10 mg KOH/g, at which point an addition of short chain fatty acids (<C12) occurred and the reaction was continued until the hydroxyl value is below 5 mg KOH/g. Excess fatty acid and volatile reaction byproducts were then removed via short path distillation under vacuum and elevated temperature. Common ester purification techniques may be utilized in the absence of short path distillation. The ester product of the reaction was purified to an acid value <1 mg KOH/g with a preferred acid value <0.5 mg KOH/g, and a hydroxyl value <10 mg KOH/g with a preferred hydroxyl value <5 mg KOH/g.

TMP is trimethylolpropane. PG ## is a propoxylated glycerol ester with an average degree of propoxylation=##. C8-C10 is a topped fraction of coconut oil. C12 is lauric acid. Pamolyn is a commercial fatty acid that is high in oleic acid and derived from tall oil. BFT is oleic acid derived from bleachable fancy tallow. HOSO is high oleic soybean oil. SBO is soybean oil. EH is 2-ethylhexanoic acid. C18 Iso is isostearic acid. HSA is 12-hydroxystearic acid. EG ## is an ethoxylated glycerol ester with an average degree of ethoxylation=##.

Examples 89-91 see FIG. 15: Proton NMR was performed to evaluate the strength of the hydrogen bonds at the glycerol, propoxylated glycerol ester, and TMP base oils. High electron density around a proton stabilizes its bond to the adjacent carbon atom and correlates to NMR absorbance at a lower ppm value. Electronegative groups attached to the C—H system decrease the electron density around the protons and increase their chemical shift to higher ppm values. The $^{1}$H NMR peaks, see FIG. 16, Table 2, of the alpha-methine and beta-methylene protons of the glycerol ester, see FIG. 14, show a shift to lower ppm compared to the methylene and methine protons of the glycerol backbone on the propoxylated glycerol ester, see FIG. 1, indicating an increase in electron density at these positions which correlates to higher stability for the proton(s). The increased electron density observed from the $^{1}$H NMR of the propoxylated glycerol ester is due to the electron-donating properties of the ether linkages of the propoxy groups. The protons with the lower chemical shift are expected to be less reactive and have greater thermal stability than their higher value counterparts. TMP was included as a reference due to its inherent thermal stability having no beta proton.

Examples 98 and 103, see FIG. 17, Table 3: Rotating Pressure Vessel Oxidation Test (RPVOT) was performed to evaluate the thermo-oxidative and hydrolytic stability of natural glycerol ester, propoxylated glycerol ester, and TMP ester base oils as specified in ASTM D2272. Additives were not added to the base oils; however, the natural oils would have naturally occurring antioxidants. Example 98, an unsaturated propoxylated glycerol ester with a viscosity grade of 68, showed a RPVOT lifetime of 28 minutes while Example 103, a saturated propoxylated glycerol ester with a viscosity grade of 58, had an RPVOT lifetimes of 31 min. For comparison, soybean oil and Canola oil were tested. The unsaturated propoxylated glycerol ester exhibits a 64% increase in the RPVOT lifetime compared to the best performing natural glycerol ester and the saturated propoxylated glycerol ester exhibits an 82% increase. Unexpectedly, the performance of the propoxylated glycerol ester significantly exceeds the RPVOT lifetime of TMP trioleate. See, *Lubrication Science,* 2015, 27(6), p 369.

Examples 91, 92, 103, 90, see FIG. 18, Table 4: In addition to thermo-oxidative stability, hydrolytic stability is often seen as a weakness in ester base oils. The data for hydrolytic stability testing (ASTM D2619) of several saturated ester base oils can be seen in Table 4, see FIG. 18. Saturated esters were used to determine the inherent stability of the ester without confounding factors (unsaturation and secondary oxidation products). The propoxylated glycerol ester base oil sample (Ex. 91 and 103) shows greater resistance to hydrolysis than glycerol esters (Ex. 92) and TMP esters (Ex. 90). Reduced hydrolysis indicates increased stability in the presence of water, heat, and catalyst and is supported by RPVOT lifetime data.

In combined cycle units, new designs include the steam, gas turbine and generator on a single shaft. As such, the lubricant will need to withstand the operating conditions of steam (wet) and gas (hot). See, *Fuels and Lubricants Handbook*, pp. 582-583.

Examples 90, 92-94: Reductions in the enthalpy of melting are observed for propoxylated glycerol esters and TMP esters relative to the glycerol ester, see FIG. 19, Table 5, FIG. 20, Table 6 and FIG. 21, Table 7. Example 94 (PG10 derivative) possesses the greatest reduction in melt enthalpy and the lowest degree of undercooling for C12 esters in FIG. 19, Table 5. DSC analysis was conducted within the temperature range −80° C. to 40° C. with cyclic cooling and heating rates of 5° C./min. The DSC melt thermograms for each material were integrated as a function of temperature and normalized to the overall melt enthalpy to generate a percent solids index that is the basis for the data in the Solids @ Onset+T columns. The data under Solids @ Onset+5 and +10° C. are indicative of the percent of solids in a base oil when heating from a fully solid or crystalline state. At 10° C. above the onset temperature, both the glycerol ester, Example 92, and neopentyl polyol ester (TMP), Example 90, show significant amounts of crystalline solids which can be expected to cause issues within a lubrication system. Both glycerol and TMP esters show higher degrees of undercooling and higher melt enthalpies compared to analogous propoxylated glycerol esters, see FIG. 20, Table 6.

Examples 91, 95-98, 100, 107, 109: Alteration of the fatty acid component of the esters has a clear effect on the melt enthalpy, cloud point, and pour point, see FIG. 21, Table 7. Materials that form a well-defined crystal structure appear opaque under visual inspection below the pour point. Less ordered or structured materials appear translucent or transparent when observed at temperatures below their pour point and require less heat to melt. Unexpectedly, the base oils of this disclosure can be modified such that the solid structure of the material can range from opaque crystalline solid to transparent amorphous solid. This is accomplished by propoxylation of the glycerol and esterifying it with mono- and polyunsaturated fatty acids (Example 98 and 100), low melt-point saturated fatty acids (Example 91), branched fatty acids (Example 107), and/or diacids (Example 109). It is important to note that there are applications which require lubricants and greases to maintain transparency in cold climates. A transparent solid allows for the inspection of the article to which the oil or grease has been applied. This is known to be of value for applications in wire rope lubrication where it is critical that the wire can be inspected for damage. Additionally, in these applications, it is usually desirable for the lubricant or grease to be an environmentally acceptable lubricant.

Examples 90, 98-104 see FIG. 22, Table 8: Representative base oils derived from propoxylated glycerol (PG10) and whole cut, or substantially whole cut, fatty acid sources. All examples have pour points and viscosities representative of lubricating base oils in ISO VG 46-68 and SAE30. All samples exhibit very high viscosity indices (>180), and Examples 91, 98, and 100 remain transparent below their pour points as indicated by no observed cloud point.

Example 103 see FIG. 23, Table 9: One iteration of the base oil of this disclosure, Example 103, was tested for biodegradability according to OECD 301B. The sample was found to exhibit "Ready biodegradability in an aerobic aqueous medium" with 61% biodegradation at the end of the 10-day window.

Example 103 and 98 see FIG. 24, Table 10: Biobased Carbon Analysis. Examples 103 and 98 were characterized using ASTM method D6866-20 to determine the % Biobased Carbon that composes the base oil. The variation in the biobased carbon content is based on the degree of alkoxylation and the fatty acid carbon number.

Examples 105-109 see FIG. 25, Table 11: Base oils that utilize branched, functional, and diacid species to alter physical properties of the base oils. All examples retain low pour points, representative viscosities, and high viscosity indices. Examples 107-109 expand the potential range of applications as they match ISO VG 100 and 150 oils. The higher viscosity oils would be prime candidates as base oils for greases and gear oils.

Example 103 (Formulated) see FIG. 26, Table 12: One iteration of the base oil of this disclosure, Example 103, was formulated using commercially available antioxidant, anti-corrosion, and anti-wear additive packages for use as turbine oil and as hydraulic/universal tractor fluid (additive packages supplied by Tiarco Chemical and King Industries, respectively). The two formulations of the base oil were then compared using common bench tests to Chevron GST (ISO VG 68) and to a formulated soybean oil and a formulated canola oil using King Industries NA-Lube BL-1208 additive system. Chevron GST was included as an industry leading turbine oil suited for use in gas, steam, and hydropower turbines, as well as in hydraulic controls within hydropower facilities.

Examples 110-112 see FIG. 27, Table 13: Ethoxylated glycerol ester properties. Ethoxylated glycerol (EG12, Lumulse 12 from Vantage Oleochemical) wherein the molecule has an average of 12 ethoxy groups was esterified with coconut fatty acid (Example 110), lauric acid (Example 11), via Method A. Table 13 compares the ethoxylated glycerol esters to the propoxylated glycerol esters with similar fatty acid sources. Example 112 is a propoxy-ethoxylated glycerol ester trioleate produced using Method A. The DO capped propoxylated glycerol (PG10EGc, Carpol 725 from Carpenter Chemical) is a glycerol with an average of 10 propoxy groups where each terminal propoxy group is capped with one ethoxy group (3 DO per molecule).

Various modifications and variations of the described methods and compositions will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

What is claimed is:

1. A synthetic ester base oil comprising:

greater than 5 percent by weight a fully esterified reaction product of:

an alkoxylated glycerol with an average degree of alkoxylation ≥3 wherein at least one alkoxylate is a propoxylate or a butoxylate repeat unit; and at least one fatty acid having ≥8 carbon atoms.

2. The synthetic ester base oil of claim 1, where thermo-oxidative stability of the synthetic ester base oil is increased by greater than 25% as determined by RPVOT lifetime via ASTM D2272 compared to a glycerol ester of the same and fatty acid composition and no alkoxylation.

3. The synthetic ester base oil of claim 1, where the hydrolytic stability, determined via ASTM D2619, of the base oil is improved as measured by the reduction of the total acid value number by greater than 50% relative to a glycerol ester having a same fatty acid composition and no alkoxylation.

4. The synthetic ester base oil of claim 1, wherein melting enthalpy, measured in J/g via a differential scanning calorimeter, has been decreased by over 50% relative to a glycerol ester having a same fatty acid composition and no alkoxylation.

5. The synthetic ester base oil of claim 1, wherein melting enthalpy has been decreased such that the synthetic ester base oil does not exhibit a detectable cloud point and remains translucent as there is no increase in opaqueness in the synthetic ester base oil due to a lack of a clouding point.

6. The synthetic ester base oil of claim 1, wherein the alkoxylate is derived from ethylene oxide, propylene oxide, butylene oxide, or a combination thereof.

7. The synthetic ester base oil of claim 6, wherein the alkoxylated glycerol is propoxylated glycerol with from 3 to 20 propoxy groups.

8. The synthetic ester base oil of claim 1, wherein at least one fatty acid is a dicarboxylic acid.

9. The synthetic ester base oil of claim 1, wherein at least one fatty acid is a linear saturated or unsaturated acid.

10. The synthetic ester base oil of claim 1, wherein at least one fatty acid is derived from a whole cut or substantially whole cut fatty acid.

11. The synthetic ester base oil of claim 1, wherein at least one fatty acid is a functionalized acid.

12. The synthetic ester base oil of claim 1, wherein at least one fatty acid is branched.

13. The synthetic ester base oil of claim 1, wherein the base oil is not less than 50 percent biodegradable in the 10-day window of OECD 301B test.

14. The synthetic ester base oil of claim 1, wherein the base oil is at least 40 percent biobased carbon.

15. A synthetic lubricant comprising the synthetic ester base oil of claim 1 incorporating at least one additive selected from an antioxidant, an anti-wear agent, an anti-corrosion agent, an anti-sludge agent, an anti-foam agent, a demulsifier, a viscosity index improver agent, a detergent/dispersant, a pour-point depressants, an alkalinity improver, a friction modifier, a seal swell agent, a metal deactivator/complexing agent, and/or an extreme pressure agent.

16. The synthetic ester base oil of claim 15, where thermal oxidative stability, as determine by RPOVT lifetime is greater than 600 minutes.

17. The synthetic ester base oil of claim 1, further comprising a hydrolytically stable, biodegradable lubricant.

18. The synthetic ester base oil of claim 17, wherein the alkoxylated glycerol ester has hydrolytic stability and biodegradation by tailoring ester bond stability and ester density through use of alkoxylation wherein degradation products of the alkoxylated glycerol ester are nontoxic.

19. The synthetic ester base oil of claim 17, wherein the lubricant viscosity is from 32-150 $mm^2/s$ at 40° C.

20. The synthetic ester base oil of claim 1, further comprising an ester of an alkoxylated glycerol with an average degree of alkoxylation ≥5.

* * * * *

UNITED STATES PATENT AND TRADEMARK OFFICE

CERTIFICATE OF CORRECTION

PATENT NO. : 11,680,218 B2
APPLICATION NO. : 17/115934
DATED : June 20, 2023
INVENTOR(S) : Zachary J. Hunt et al.

It is certified that error appears in the above-identified patent and that said Letters Patent is hereby corrected as shown below:

In the Specification

The government support clause, add the following paragraph to read as follows:
This invention was made with government support under 2019-33610-30170 awarded by the National Institute of Food and Agriculture. The government has certain rights in the invention.

Signed and Sealed this
Fourteenth Day of May, 2024

Katherine Kelly Vidal

Katherine Kelly Vidal
*Director of the United States Patent and Trademark Office*